(12) United States Patent
Cromwell et al.

(10) Patent No.: US 8,394,032 B2
(45) Date of Patent: Mar. 12, 2013

(54) INTERPRETIVE REPORT IN AUTOMATED DIAGNOSTIC HEARING TEST

(75) Inventors: Daniel Cromwell, Spring, TX (US); Linda Galow, Houston, TX (US); Kenneth R. Stott, Charlotte, NC (US)

(73) Assignee: Tympany LLC, The Woodlands, TX (US)

(*) Notice: Subject to any disclaimer, the term of this patent is extended or adjusted under 35 U.S.C. 154(b) by 383 days.

(21) Appl. No.: 12/356,507

(22) Filed: Jan. 20, 2009

(65) Prior Publication Data

US 2009/0177113 A1  Jul. 9, 2009

Related U.S. Application Data

(63) Continuation of application No. 11/469,461, filed on Aug. 31, 2006, now abandoned, and a continuation-in-part of application No. 10/942,712, filed on Sep. 16, 2004, now Pat. No. 7,736,321, and a continuation-in-part of application No. 10/663,225, (Continued)

(51) Int. Cl.
*A61B 5/00* (2006.01)

(52) U.S. Cl. .......................................... 600/559; 73/585
(58) Field of Classification Search .................. 600/559; 73/585

See application file for complete search history.

(56) References Cited

U.S. PATENT DOCUMENTS

| | | | |
|---|---|---|---|
| 3,054,855 A | 9/1962 | Hyman | |
| 3,134,861 A | 5/1964 | Dempsey | |
| 3,623,241 A | 11/1971 | Horner et al. | |
| 4,284,847 A * | 8/1981 | Besserman | ...................... 73/585 |
| 5,197,332 A | 3/1993 | Shennib | |
| 5,323,468 A | 6/1994 | Bottesch | |
| 5,645,074 A | 7/1997 | Shennib et al. | |
| 5,811,681 A | 9/1998 | Braun et al. | |
| 6,160,893 A | 12/2000 | Saunders et al. | |
| 6,168,563 B1 | 1/2001 | Brown | |

(Continued)

FOREIGN PATENT DOCUMENTS

| | | |
|---|---|---|
| GB | 2351838 | 1/2001 |
| JP | 05030599 | 2/1993 |

(Continued)

OTHER PUBLICATIONS

European Supplementary Search Report for Corresponding European Patent Application EP04752359.2.

(Continued)

*Primary Examiner* — Max Hindenburg
(74) *Attorney, Agent, or Firm* — Locke Lord LLP

(57) ABSTRACT

A multimedia user interface for an automated diagnostic hearing test allows a patient to interact with the automated hearing test in order to conduct various hearing related tests. The patient is given instructions and guidance for every test, and can call the operator at any time for help. Warning messages and progress indicators are provided to help the patient gauge his progress. This allows the patient to test his own hearing with minimal or no assistance from an audiologist or other hearing health professional. The user interface also allows the operator to configure and customize the automated hearing test as needed. The results of the hearing related tests are summarized in a single report that is concise, convenient, and thorough. The report may include interpretive comments that point out possible inconsistencies, asymmetries, or areas of concern in the test results and, where appropriate, also recommend certain types of medical treatment.

9 Claims, 22 Drawing Sheets

Related U.S. Application Data filed on Sep. 16, 2003, now Pat. No. 7,288,072, which is a continuation-in-part of application No. 10/439,958, filed on May 15, 2003, now Pat. No. 7,695,441.

(60) Provisional application No. 60/713,538, filed on Aug. 31, 2005, provisional application No. 60/504,079, filed on Sep. 19, 2003, provisional application No. 60/466,313, filed on Apr. 29, 2003, provisional application No. 60/383,303, filed on May 23, 2002.

(56) References Cited

U.S. PATENT DOCUMENTS

| | | | |
|---|---|---|---|
| 6,201,875 B1 | 3/2001 | Davis et al. | |
| 6,331,164 B1 | 12/2001 | Shaw et al. | |
| 6,366,863 B1 | 4/2002 | Bye et al. | |
| 6,377,925 B1 | 4/2002 | Greene et al. | |
| 6,379,314 B1 | 4/2002 | Horn | |
| 6,396,930 B1 | 5/2002 | Vaudrey et al. | |
| 6,416,482 B1 | 7/2002 | Braun et al. | |
| 6,428,485 B1 | 8/2002 | Rho | |
| 6,447,461 B1* | 9/2002 | Eldon | 600/559 |
| 6,496,585 B1* | 12/2002 | Margolis | 381/60 |
| 6,644,120 B1 | 11/2003 | Braun et al. | |
| 6,647,345 B2 | 11/2003 | Bye et al. | |
| 6,674,862 B1 | 1/2004 | Magilen | |
| 6,730,041 B2 | 5/2004 | Dietrich | |
| 7,450,724 B1* | 11/2008 | Greminger | 381/60 |
| 2001/0049480 A1 | 12/2001 | John et al. | |
| 2002/0016554 A1 | 2/2002 | Iseberg | |
| 2002/0026091 A1* | 2/2002 | Leysieffer | 600/25 |
| 2002/0026125 A1 | 2/2002 | Leysieffer | |
| 2002/0068986 A1 | 6/2002 | Mouline | |
| 2002/0076056 A1 | 6/2002 | Pavlakos | |
| 2002/0107692 A1 | 8/2002 | Litovsky | |
| 2002/0136365 A1 | 9/2002 | D'Agri | |
| 2002/0165466 A1 | 11/2002 | Givens et al. | |
| 2003/0083591 A1 | 5/2003 | Edwards et al. | |
| 2004/0006283 A1 | 1/2004 | Harrison et al. | |
| 2004/0039299 A1 | 2/2004 | Harrison et al. | |
| 2004/0049125 A1 | 3/2004 | Nakamura | |
| 2004/0064066 A1 | 4/2004 | John et al. | |
| 2004/0068200 A1 | 4/2004 | Harrison et al. | |
| 2004/0071295 A1 | 4/2004 | Wasden et al. | |
| 2004/0071296 A1 | 4/2004 | Wasden et al. | |
| 2004/0073134 A1 | 4/2004 | Wasden et al. | |
| 2004/0073135 A1 | 4/2004 | Wasden et al. | |
| 2004/0073136 A1 | 4/2004 | Thornton et al. | |
| 2004/0097826 A1 | 5/2004 | Harrison et al. | |
| 2004/0097839 A1 | 5/2004 | Epley | |
| 2004/0152998 A1 | 8/2004 | Stott et al. | |
| 2005/0033193 A1 | 2/2005 | Wasden et al. | |

FOREIGN PATENT DOCUMENTS

| | | |
|---|---|---|
| NL | 8400196 | 8/1984 |
| WO | 8707464 | 12/1987 |
| WO | 9841973 | 9/1998 |
| WO | 0065983 | 11/2000 |
| WO | 0106916 | 2/2001 |
| WO | 02062221 | 8/2002 |
| WO | 2004/104761 | 12/2004 |
| WO | 2004104761 | 12/2004 |

OTHER PUBLICATIONS

International Search Report for Corresponding International Application No. PCT/US03/16200.
International Search Report for Corresponding International Application No. PCT/US04/15329.
Written Opinion for Corresponding International Patent Application No. PCT/US04/15329.
International Search Report for Corresponding International Application No. PCT/US04/15328.
Written Opinion for Corresponding International Patent Application No. PCT/US04/15328.
International Search Report for Corresponding International Application No. PCT/US06/34324.
Written Opinion for Corresponding International Patent Application No. PCT/US06/34324.
International Search Report for Corresponding International Application No. PCT/US06/34357.
Written Opinion for Corresponding International Patent Application No. PCT/US06/34357.
McCullough et al., "A multimedia approach for estimating speech recognition of multilingual clients.", AJA, Mar. 1994, p. 19-22.
Matsuhira, T., "Improved method of masking in pure tone audiometry—use of minimum level masking." Practica Ota-Rhino-Laryngologica, 82:11; p. 1540-1541, 1989.
Smith, B. and Markides, A., "Interaural attenuation for pure tones and speech." British Journal of Audiology, 15:40, p. 9-54, 1981.
Thornton, A., "Computer-Assisted Audiometry and Technicians in a High-Volume Practice." Nov. 1993, AJA, p. 11-13.
Barry, S., "Can Bone Conduction Thresholds Really Be Poorer Than Air?" Nov. 1994, AJA, p. 21-22.
Dean, M. and Martin F., Insert Earphone Depth and the Occlusion Effect, AJA, vol. 9, 159-0889, Sep. 5, 2000.
McCcullough, J., Wilson, R., Birck J., and Anderson, L., A Multimedia Approach for Estimating Speech Recognition of Multilingual Clients, Mar. 1994, AJA, p. 19-22.
Wilson, R. and Antablin, J., "A Picture Identification Task as an Estimate of the Word-Recognition Performance of Nonverbal Adults." Journal of Speech and Hearing Disorders, May 1980, vol. 45, No. 2.
Studebaker, G., et al. "Frequency—Importance and Transfer Functions for Recorded CID-W-22 Word Lists." Journal of Speech and Hearing Research, Apr. 1991, vol. 34, p. 427-438.
Thornton, A., et al. Speech-Discrimination Scores Modeled as a Binomial Variable, Journal of Speech and Hearing Research, Sep. 1978, vol. 21, No. 3, p. 507-518.
Haplin , C., "The articulation index in clinical diagnosis and hearing aid fitting." Current Opinion in Otalaryngology & Head and Neck Surgery, 1996, Rapid Science Publishers, p. 325-334.
International Search Report for Corresponding International Application No. PCT/US03/16180.
European Search Report for Corresponding European Patent Application EP03755440.9.
European Supplementary Search Report for European Patent Application No. 04752358.4, dated Apr. 24, 2009.
Clevorn, J., Supplementary European Search Report for European Patent Application No. 06814100.1, European Patent Office, Berlin, dated Jun. 22, 2011.
Altshuler, M.W., "The Stenger Phenomenon," Journal of Communication Disorders, vol. 3, No. 2, 1970, pp. 89-105.
"The Audiology Primer for Students and Health Care Professionals." Department of Veterans Affairs, Summer, 1997, p. i-69.
Australian Search Report for Corresponding Australian Patent Application No. 2006287194.
EPO Search Report for Corresponding European Patent Application No. EP99300.
Monro, D. A. et al., "Effects of Sophistication on 4 Tests for Nonorganic Hearing Loss," Journal of Speech and Hearing Disorders, America Speech and Hearing Assoc., Danville, IL, US, vol. 42, No. 4, Nov. 1, 1977, pp. 528-534.
Oeken, J et all., "Objektive Methoden zum Simulationsnachweis einer einseitigen Taubheit unter besonderer Berucksichtigung der DPOAE am Beispiel einer Kasuistik," HNO, vol. 46, No. 4, Apr. 1, 1998, pp. 348-353.
Rogers, J., "Audiology Policy for Stenger Screening Test." Conwy & Denbighshire NHS Trust. Apr. 2002 [retrieved on Apr. 3, 2007]. Retrieved from the Internet: <URL:http://www.glanclwyd.demon.co.uk/audiology/clinprot/stengerscreeningpolicy.htm>, entire document.
Watson, J. E., et al., "A Report on the Use of the Bekesy Aduiometer in the Performance of the Stenger Test," Journal of Speech and Hearing Assoc., Danville, IL, US, vol. 29, No. 1, Feb. 1, 1964, pp. 36-46.

* cited by examiner

520

```
Otogram Configuration
| Input Screen | Paging Encoder Interface | Paging Options | Machine Options | Reporting Options | Network Options | Test Options |
```

522 — ☑ Paging Encoder is Attached

524:
- Communications Port: 1
- Encoder ID: WaveWare Paging Encoder
- Encoder Timeout: 500
- Pager CapCode: 0000100
- Pager Data Rate: 5

[ Save ] [ Exit ]

```
Otogram Configuration
| Input Screen | Paging Encoder Interface | Paging Options | Machine Options | Reporting Options | Network Options | Test Options |
```

Page Format [%N-Patient Name, %T-Test Name.]

532 — ☑ Page Administrator at end of testing session — %N's Otogram is completed.
534 — ☐ Page Administrator at end of each test — %N has completed the %T test.
536 — ☑ Page Administrator after inactivity threshold — %N is not progressing through the %T test.
  Inactivity Threshold (in seconds): 120
538 — ☑ Page Administrator after inability to reach pure tone threshold — %N is not progressing through the %T test.
  Inability Threshold (in seconds): 360

} 539

540 — Paging Device: Radio
542 — Network Paging Drop: [          ]

[ Save and Exit ] [ Exit ]

| | Name | Conductive Loss | | Chart# | 000 |
|---|---|---|---|---|---|
| | Date | 02/23/2005 | | Doctor | Dr. Suess |
| | Time | 11:05 | | Tester | Mary |
| | DOB | W/Masking Dilemma | | Clinic | Unknown |
| Version: 2.0.29 | Sex | | | Elapsed | Session2099 TAR:. PT:14.5 SRT:. SD: 1104 |

Test Summary

| Test Type | Right Ear | Left Ear |
|---|---|---|
| Pure Tones | Moderate - Severe Mixed Hearing Loss | Severe - Profound Mixed Hearing Loss |
| Air Threshold Asymmetry | 250Hz 500Hz 1000Hz 2000Hz 4000Hz | |

Audiogram Results indicate Patient has Moderate - Severe Mixed Hearing Loss in the RIGHT ear, and Severe - Profound Mixed Hearing Loss in the LEFT ear. Air Threshold Asymmetry occurred at the following frequencies: 250Hz 500Hz 1000Hz 2000Hz 4000Hz.

Medical Recommendations

| Medical Referral / Treatment | Retest or referral may be needed |
|---|---|
| Amplification Requirements | Reassess after Referral / Treatment |
| Conservation / Hearing Protection | Recommended |
| Retest | 1 year |

Case History

| Do you experience any of the following: | Right Ear | Left Ear | Comments |
|---|---|---|---|
| Ringing or other noises in the ears (Tinnitus) | Yes / No | Yes / No | |
| Visible congenital or traumatic deformity of the ear | Yes / No | Yes / No | |
| History of active drainage from the ear within the previous 90 days | Yes / No | Yes / No | |
| Current hearing aid user | Yes / No | Yes / No | |
| History of sudden or rapidly progressive hearing loss within the previous 90 days | Yes / No | Yes / No | |
| Acute or chronic dizziness | Yes / No | | |
| Feeling of fullness in the ears | Yes / No | Yes / No | |
| Unilateral hearing loss of sudden or recent onset within the previous 90 days | Yes / No | Yes / No | |
| Audiometric air-bone gap equal to or greater than 15 decibels at 500 Hz, 1000 Hz, and 2000 Hz | No | No | |
| Visible evidence of significant cerumen accumulation or a foreign body in the ear canal | Yes / No | Yes / No | |
| Pain or discomfort in the ears | Yes / No | Yes / No | |

Medical Release (To be completed by a Medical Doctor)

Note: If a patient has any warning signs as identified above, then a referral to licensed physician who specializes in disease of the ear is necessary.

( ) Refer to an ear specialist OR ( ) The Patient _____ has been medically evaluated and has no contra-indications and may be considered as a candidate for the use of hearing aids.

Physician Signature:_____ Date:_____ HHN Fax Number: 877-582-5032

FIG. 11C

INTERPRETIVE REPORT IN AUTOMATED DIAGNOSTIC HEARING TEST

CROSS-REFERENCE TO RELATED APPLICATIONS

This application is a continuation of application Ser. No. 11/469,461, filed Aug. 31, 2006, which claims the benefit of priority to Provisional Application No. 60/713,538, filed Aug. 31, 2005; and is a continuation-in-part of application Ser. No. 10/942,712, filed Sep. 16, 2004, which claims the benefit of priority to Provisional Application No. 60/504,079, filed Sep. 19, 2003; and which is a continuation-in-part of application Ser. No. 10/663,225, filed Sep. 16, 2003, which is a continuation-in-part of application Ser. No. 10/439,958, filed May 15, 2003, which claims the benefit of priority to Provisional Application No. 60/383,303, filed May 23, 2002, and Provisional Application No. 60/466,313, filed Apr. 29, 2003. All of the above applications are hereby incorporated by reference herein in their entirety.

FIELD OF THE INVENTION

This invention is directed in general to the field of audiology and in particular to a user interface for an automated method and system of assessing and analyzing hearing loss.

DESCRIPTION OF THE RELATED ART

According to recent studies, over 20 million people in the United States alone have some degree of hearing loss. The number of people worldwide who have some degree of hearing loss is estimated to be much greater. Not surprisingly, many of these people are unaware that they have suffered a decrease in hearing capacity. The decreased hearing capacity may be due to several factors, including age, health, occupation, injury, and disease. This loss of hearing can lead to significant reductions in quality of life, impaired relationships, reduced access to employment and diminished productivity. Failure to treat the hearing loss may worsen the impact. According to the Better Hearing Institute, the annual cost in the United States in terms of lost productivity, special education, and medical care because of untreated hearing loss is approximately $56 billion. Much of this staggering cost can be reduced or prevented by early detection and treatment. Unfortunately, few people obtain regular and frequent hearing tests as a part of their routine healthcare due, in part, to the lack of a simple, convenient, and relatively inexpensive hearing test.

Traditionally, a hearing test is conducted in a clinical setting by a hearing health professional, such as an audiologist, who administers the hearing test manually. The hearing health professional controls an audiometer to produce a series of tones that each have a very specific frequency and intensity. The term "intensity" as used herein refers to the amplitude of the tone and is usually stated in decibels (dB). The tones are then conducted through a transducer, such as earphones or ear inserts, to the patient in a quiet room or sound isolation booth. For each audible tone, the patient gestures or otherwise indicates that he has heard the tone. If the tone is not audible, the patient does not respond. The hearing health professional thereafter adjusts the intensity level of the tone in preset increments until it becomes audible to the patient. By repeating this process for several different tones and compiling the results, the hearing health professional is able to determine the extent of the hearing loss, if any.

An advantage of having a hearing health professional manually administer the hearing test is the hearing health professional can apply his considerable training and experience during the test. For example, by simply talking to the patient and varying the loudness of his voice, the hearing health professional can determine an initial intensity level at which to start the tones. Furthermore, the hearing health professional can adapt the pace of the test as needed to accommodate a tired or uncooperative patient. More importantly, the hearing health professional can discern between false responses or guesses and responses that are legitimate. Finally, the hearing health professional can adjust the results of the hearing test as needed to reflect extenuating circumstances or problems, such as excessive ambient noise, equipment limitations, and other similar factors.

Like most highly trained and specialized medical professionals, however, a hearing health professional's time and services are usually expensive. Accessibility and convenience may also be issues, as there are fewer hearing health professionals relative to other types of medical professionals. And while hearing health professionals are highly trained, they are limited in their ability to make rapid and accurate calculations of the test data and must rely on approximations and rules of thumb for guidance in many instances. In addition, few hearing health professionals in the United States can speak a foreign language. As a result, traditional hearing tests are almost always administered in English, which can present a problem for non-English speaking patients.

Other drawbacks of the traditional, manually administered hearing tests include the need for a quiet room or sound isolation booth in order to properly conduct the tests. The quiet room or sound isolation booth has to comply with ANSI (American National Standards Institute) requirements in terms of how much noise may penetrate the room or booth during a test. Typically, a specially trained technician must evaluate and certify the quiet room or sound isolation booth as meeting ANSI standards before the room or booth can be used. At present, there are relatively few technicians who are trained to perform such evaluations and certifications. All the above factors combine to increase the complexity of the traditional hearing tests and thereby discourage or at least contribute to a general lack of interest by most people in obtaining regular and frequent hearing tests.

One attempt to simplify the traditional hearing test involves the use of a computer network, such as the Internet, to administer the test. The computer network facilitates interaction between a centralized test administration site and remotely located patient sites. Such an arrangement makes it possible (or at least more convenient) for people in remote or rural areas to obtain a hearing test. And the hearing test can be performed so that it meets standardized guidelines such as ANSI requirements or certification standards. Despite the increased convenience, a hearing health professional must still manually administer the test, albeit remotely. In this regard, the test is very similar to the traditional hearing test and has many of the same shortcomings.

Accordingly, what is needed is a hearing test that overcomes the shortcomings of the traditional hearing test. Specifically, what is needed is a hearing test, and a user interface therefor, that is simpler, more convenient, less expensive, can be administered by the patient instead of the hearing health professional, yet does not compromise the accuracy or thoroughness of the traditional, manually administered hearing test.

SUMMARY OF THE INVENTION

The present invention is directed to a multimedia user interface for an automated diagnostic hearing test. The user interface allows a patient to interact with the automated hearing test in order to conduct various hearing related tests. The patient is given instructions and guidance for every test, and can call the operator at any time for help. Warning messages and progress indicators are provided to help the patient gauge his progress. This allows the patient to test his own hearing with minimal or no assistance from an audiologist or other hearing health professional. The user interface also allows the operator to configure and customize the automated hearing test as needed. The results of the hearing related tests are summarized in a single report that is concise, convenient, and thorough. The report may include interpretive comments that point out possible inconsistencies, asymmetries, or areas of concern in the test results and, where appropriate, also recommend certain types of medical treatment.

BRIEF DESCRIPTION OF THE DRAWINGS

A better understanding of the invention may be had by reference to the following detailed description when taken in conjunction with the accompanying drawings, wherein:

Figures 5F, 5G:
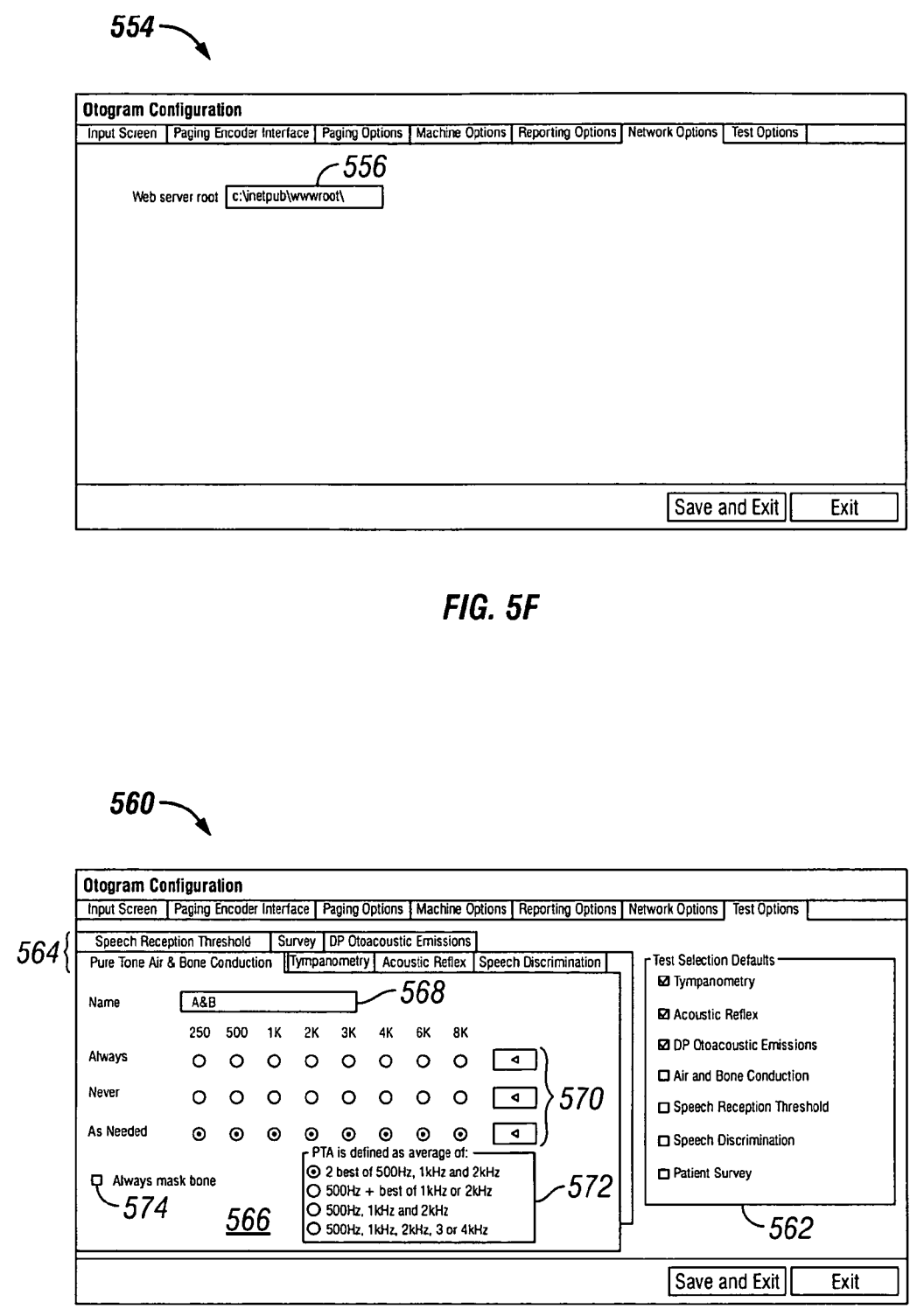
Figures 5H, 5I:
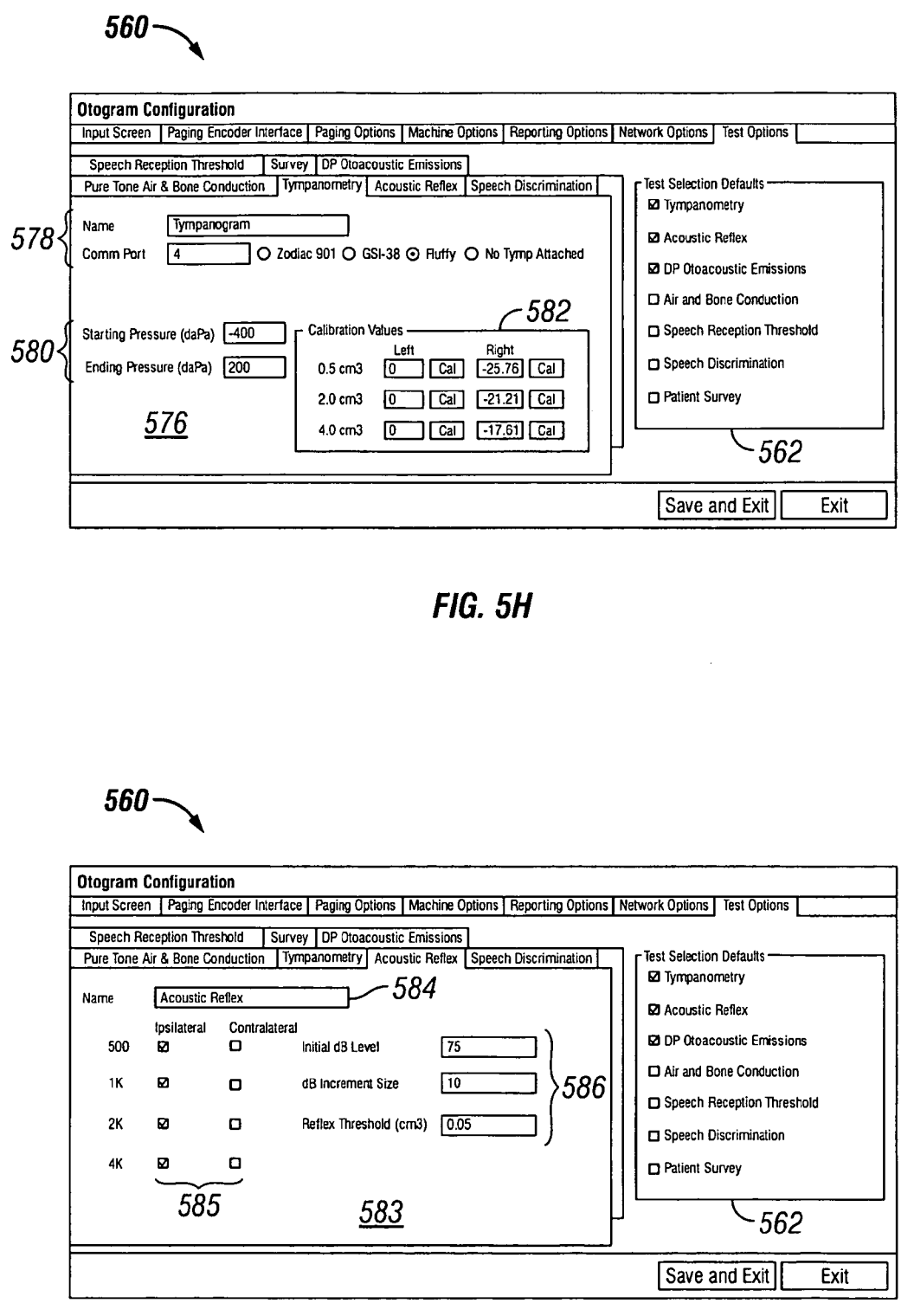
Figures 5J, 5K:
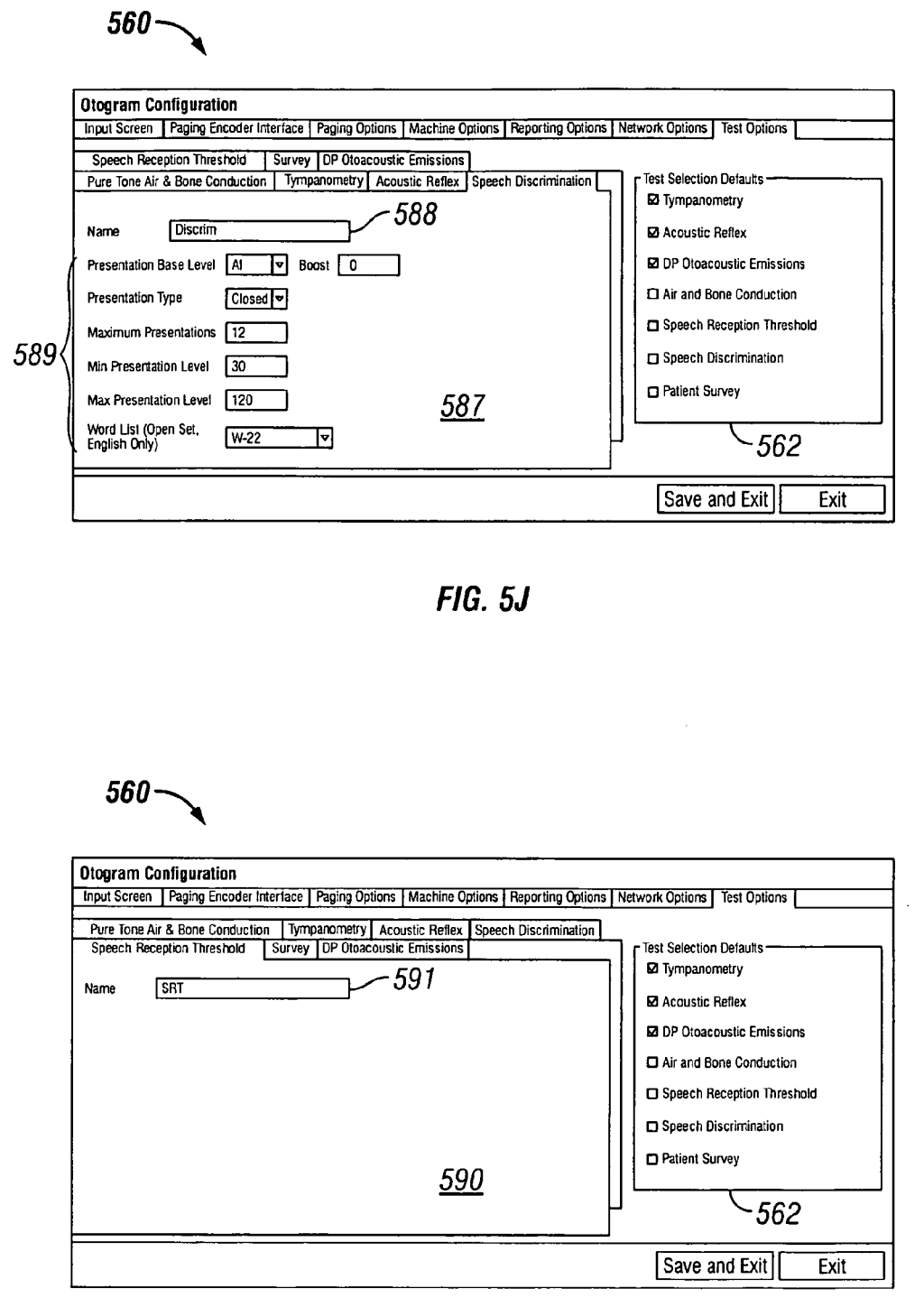
Figures 5L, 5M:
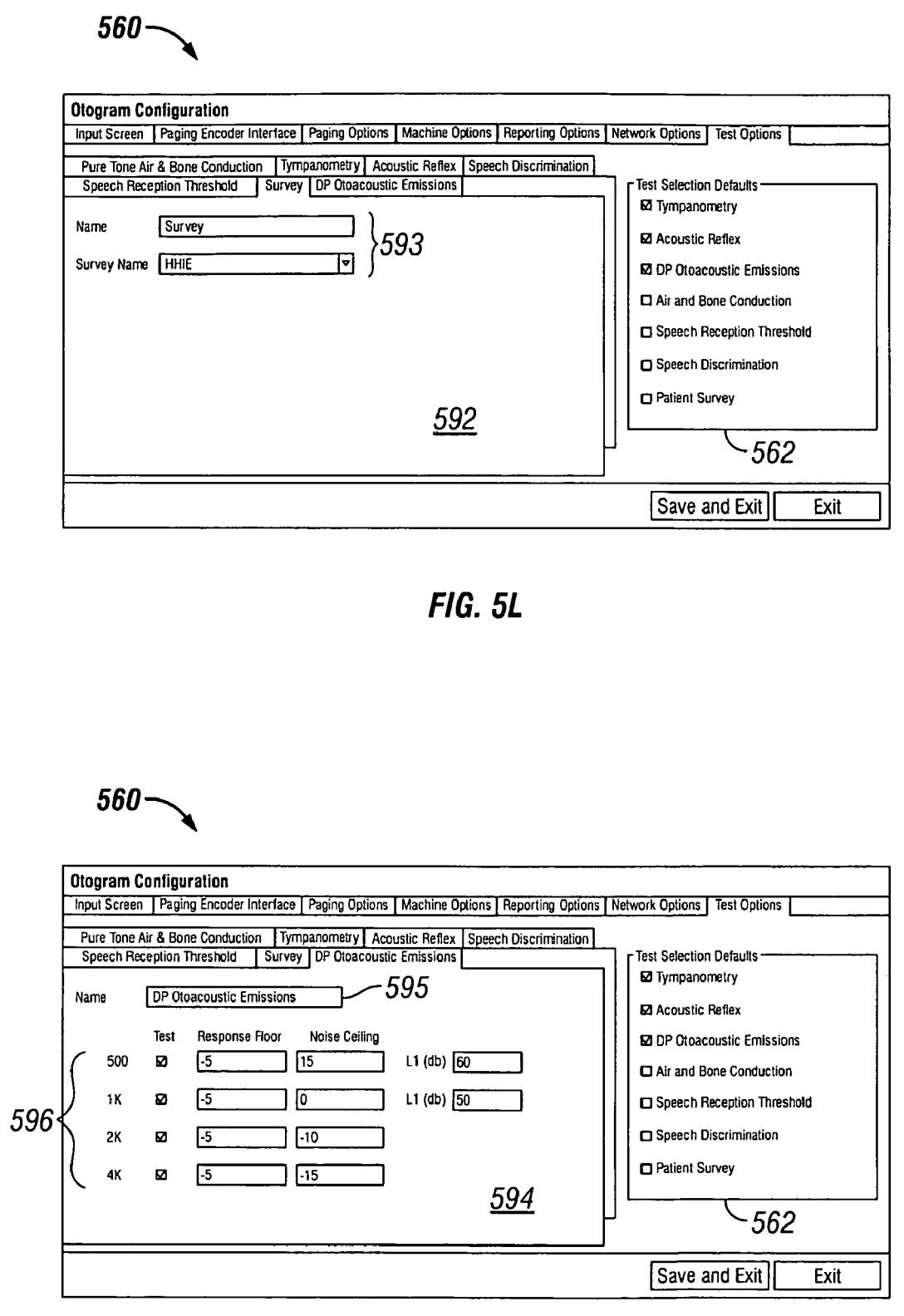

FIGS. 5A-5M illustrate an exemplary implementation of a system configuration component of the user interface according to embodiments of the invention;

FIGS. 11A-11C illustrate an exemplary hearing test report according to embodiments of the invention.

DETAILED DESCRIPTION OF THE INVENTION

Figure 1:
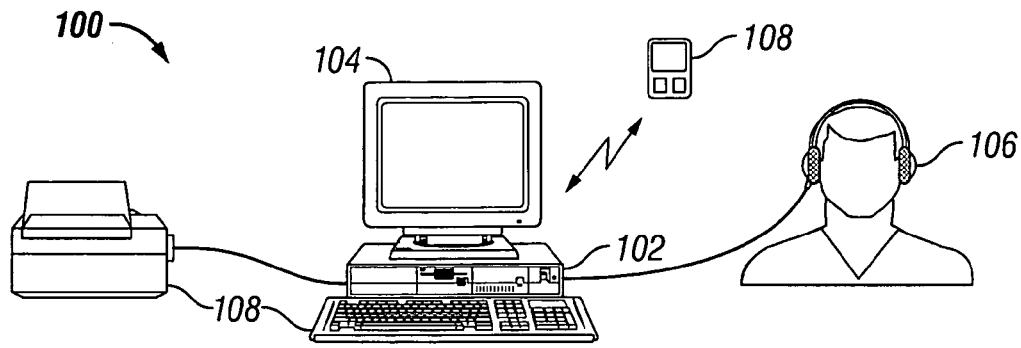
FIG. 1 illustrates an exemplary system for providing an automated hearing test according to embodiments of the invention.

Following is a detailed description of the invention with reference to the drawings wherein reference numerals for the same or similar elements are carried forward. It should be noted that unless otherwise indicated, the design and layout of the various features shown in the drawings, including the size, shape, color (or lack thereof), location, and arrangement of the various fields, checkboxes, text boxes, graphics, and other information, are provided for illustrative purposes only, and the invention is not to be limited to any particular design or layout.

As mentioned above, the present invention is directed to automated testing of a patient's hearing and, more specifically, to a user interface for such an automated hearing test. The term "automated testing" as used herein refers to testing that is performed primarily by a computer, as opposed to testing that is performed primarily by a hearing health professional. The user interface allows the patient to test his own hearing with minimal or no assistance from a hearing health professional. Typically, an operator, such as the hearing health professional or a trained administrator, helps the patient with the initial set up (e.g., seating, putting on the transducers, demonstrating button usage, etc.) and explains in general how the test works. Thereafter, the user interface instructs and prompts the patient through the remainder of the test.

Patients will realize a number of benefits from the user interface of the present invention. In general, the user interface is an intuitive, user-friendly interface that makes the automated hearing test simple to use and provides for a more pleasant and enjoyable patient experience. In addition, the user interface has a "high-tech" look and feel that inspires confidence in the patient that he is using state-of-the-art technology that will produce more accurate results. Moreover, the user interface provides a clear and consistent voice that may be easier to understand than some hearing health professionals who may speak with an accent or whose speech may otherwise be difficult to understand. Finally, the user interface allows the patient to proceed with the hearing test at his own pace, since little or no assistance is needed from the hearing health professional.

Referring now to FIG. 1, a system 100 is shown for providing automated hearing tests in which the user interface according to embodiments of the invention is used. The system 100 has three main components, namely, a computer 102, a display screen 104, and at least one transducer 106. Other components of the system 100 that may be present include a tympanometer, keyboard, mouse, printer, paging system, and the like (indicated generally at 108). The paging system may be any suitable paging technology that uses one or more pagers 108 for alerting the operator. The one or more pagers 108 preferably can display text messages for informing the operator of the nature of the alert. Other types of paging system may also be used without departing from the scope of the invention (e.g., Internet based paging systems).

The computer 102 may be any suitable computer, from a desktop PC to a high-end workstation, as the particular type/modelibrand of computer is not overly important to the practice of the invention. The display screen 104 may likewise be any suitable display screen, from a CRT to an LCD, as the particular type/modelibrand of display screen is not overly significant for purposes of the present invention. In some embodiments, however, a touchscreen monitor may be easier to use than conventional CRT or LCD display screens in terms of the physical interaction between the patient and the automated hearing test.

As for the transducer 106, this component may be an ear insert, earphones, and the like for air conduction testing. For bone conduction, the transducer 106 may be a vibrator or other similar devices. In some cases, the transducer 106 may be mounted on a headset worn by the patient. Usually, a separate transducer is used for air conduction versus bone conduction and the transducers are swapped as need during the hearing test. Preferably, the bone conduction transducer is arranged in such a way as to allow testing of either ear without moving the transducer and without interfering with the air conduction transducer. An example of a transducer that may be used with the present invention is described in U.S. patent application Ser. No. 10/438,751, entitled "Apparatus for Bone Conduction Threshold Hearing Test," which is hereby incorporated by reference.

Figure 2:
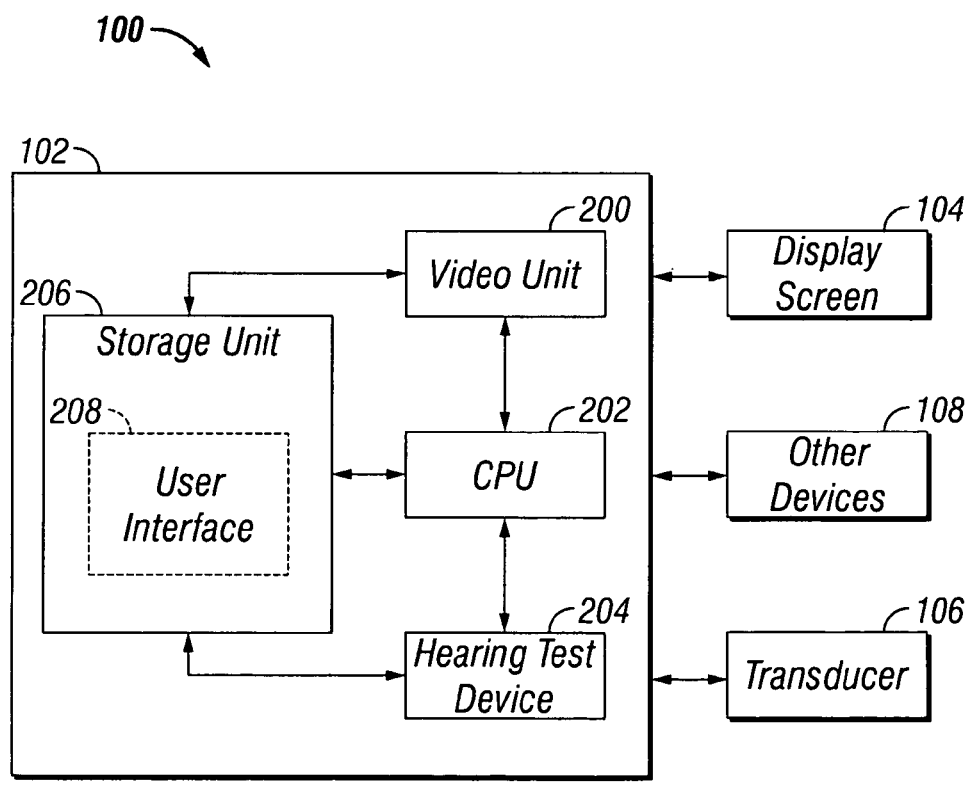
FIG. 2 illustrates a block diagram of a system having a user interface for an automated hearing test according to embodiments of the invention.

FIG. 2 illustrates the system 100 in block diagram form. As can be seen, the computer 102 has a number of functional components, including a video unit 200, a central processing unit 202, a hearing test device 204, and a storage unit 206. These components are well known in the computer art and will therefore be described only briefly here. In general, the video unit 200 provides the video signals that are displayed as images on the display screen 104. In some embodiments, the video unit 200 may be any one of several commercially available video cards. The central processing unit 202 is responsible for the overall operation of the computer 102, including execution of the operating system and any software applications residing on the computer 102. In some embodiments, the central processing unit 202 may be any one of several commercially available microprocessors. The hearing test device 204 may comprise any or all of an audiometer, an otoacoustic emission test device, a tympanometer, a masking noise generator, or other hearing test devices. In some embodiments, the hearing test device 204 may be one or more electronic circuit boards within the computer 102 for performing the functionality of such test devices. Alternatively, the hearing test device 204 may be a separate unit that is external to the computer 102. The storage unit 206 stores the automated hearing test and provides long-term and temporary (i.e., caching) storage for the software and data that are used by the computer 102 and may include one or more of, for example, a hard drive, main memory, removable storage (e.g., CD-ROM, floppy disk), and the like.

In some embodiments, the storage unit 206 also stores a multimedia user interface 208 for the automated hearing test. More specifically, the storage unit 206 stores a computer-readable version of the user interface 208 that can be executed by the computer 102. During execution, a portion of the user interface 208 may be temporarily loaded from, for example, the hard disk and into the main memory components of the storage unit 206. In addition to the stand-alone arrangement, it is also possible to execute the user interface 208 from a network. For example, the user interface 208 may be stored on a server computer (not expressly shown) that is accessible to several client computers. This arrangement has an advantage in that updates to the user interface 208 may be quickly and easily implemented for all client computers via the server computer. Other environments for executing the user interface 208 may also be used without departing from the scope of the invention.

Figure 3:
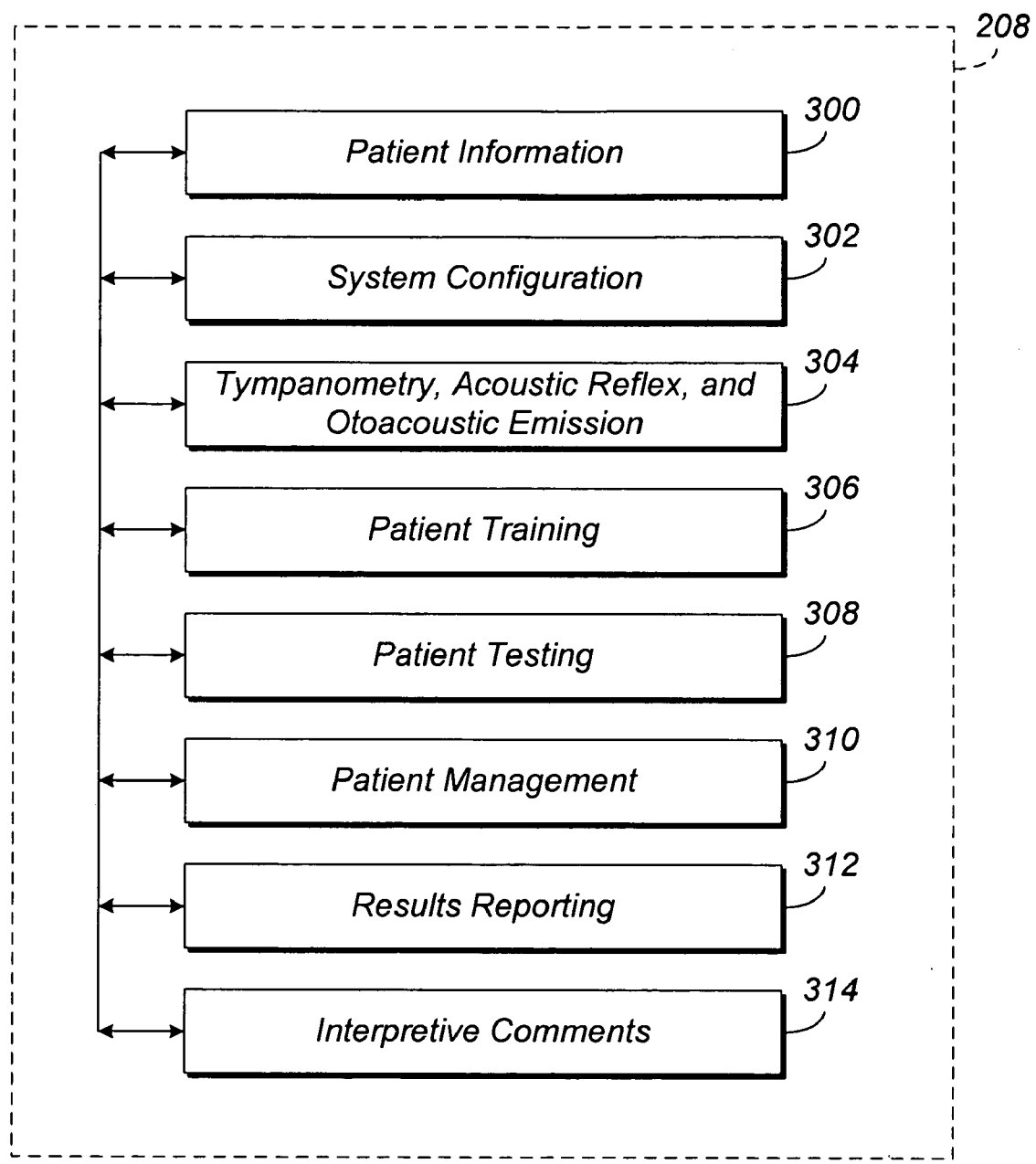
FIG. 3 illustrates an exemplary user interface for an automated hearing test according to embodiments of the invention.

FIG. 3 shows an exemplary implementation of the user interface 208. As can be seen, the user interface 208 has a number of functional components, including a patient input component 300, a system configuration component 302, a tympanogram, acoustic reflex (AR), and otoacoustic emission testing component 304, a patient training component 306, a patient testing component 308, a patient management component 310, a reporting component 312, and an interpretive comments component 314. The various functional components are typically executed in sequence as the automated hearing test progresses, but any functional component can be executed before, during, or after execution of any other functional component as needed. In addition, each functional component 300-314 may be a modular, stand-alone component that is capable of accepting data from and/or passing data to other functional components. This modularized approach allows individual functional components 300-314 to function independently of other functional components such that one or more functional components may be removed from the user interface 208 and/or inserted into another user interface (not expressly shown) with little or no modification. Operator and/or patient interaction with the user interface 208 may be accomplished using any suitable input device, for example, a mouse, keyboard, separate dedicated response button, or using a touchscreen display unit. Where a touchscreen display unit is used, the user interface 208 may display a graphical keyboard (in addition to or instead of a conventional keyboard) from which the operator and/or patient may select alphanumeric characters as needed.

Briefly, the patient information component 300 allows the operator and/or the patient to enter basic information about the patient and to select which hearing related tests to perform for the patient. The system configuration component 302 allows the operator to custom configure various aspects of the automated hearing test according to his preferences. The tympanogram, acoustic reflex, and otoacoustic emission testing component 304 facilitates obtaining a tympanogram and/or AR test for the patient. The patient training component 306 provides instructions for and guides the patient in the use of the automated hearing test prior to as well as during the actual testing. The patient testing component 308 allows the patient to interact with the automated hearing test based on the particular hearing related tests being performed (e.g., pure tone threshold, speech reception threshold, and speech discrimination). The patient management component 310 notifies the operator and/or the patient of any problems or contingencies that may arise during testing and generally helps the patient stay on course. The reporting component 312 allows the operator to view and print the results of the testing, as well as to store the results of the testing in various formats. Finally, the interpretive comments component 314 point out possible inconsistencies, asymmetries, or areas of concern in the test results and, where appropriate, recommends certain types of medical treatment. Each of the above functional components will now be described in more detail.

Figure 4:
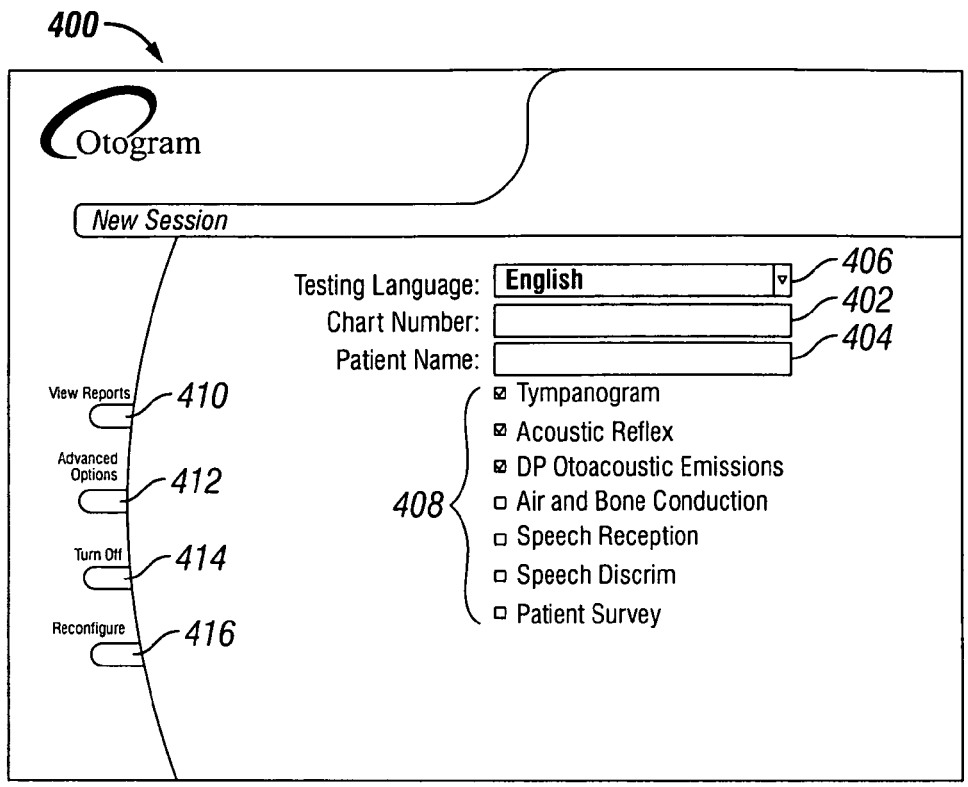
FIG. 4 illustrates an exemplary implementation of a patient input component of the user interface according to embodiments of the invention.
Figure 5A:
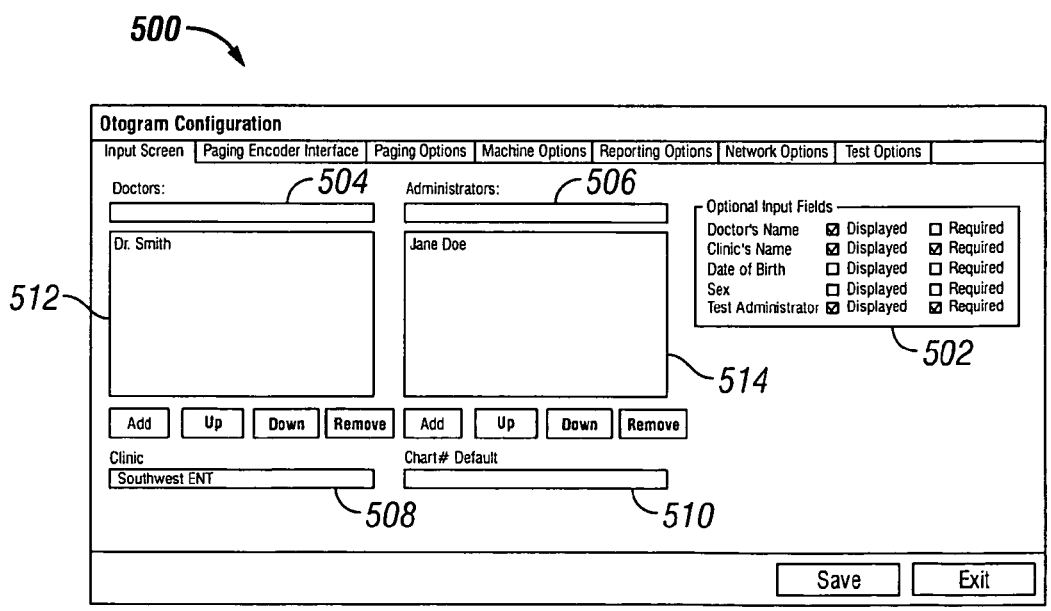
Figure 5D:
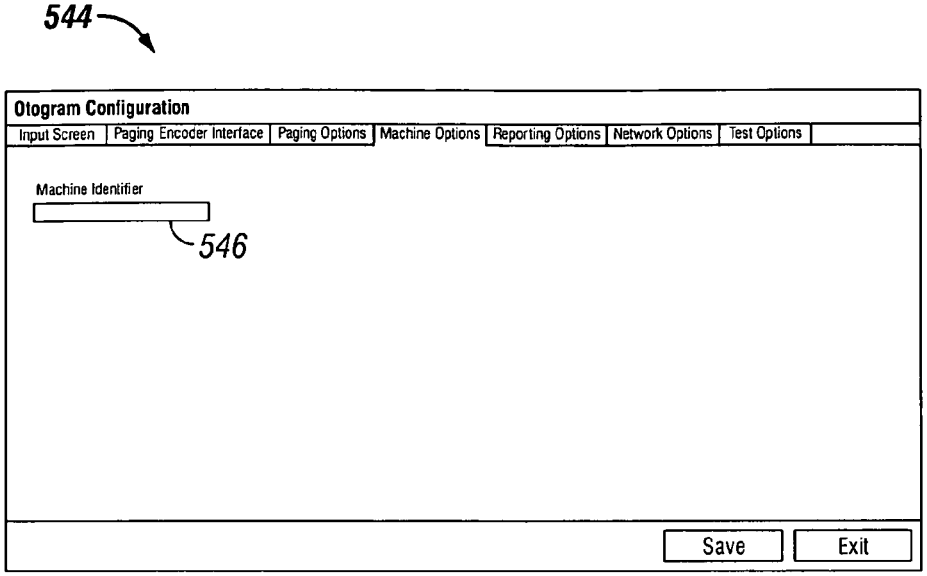
Figure 5E:
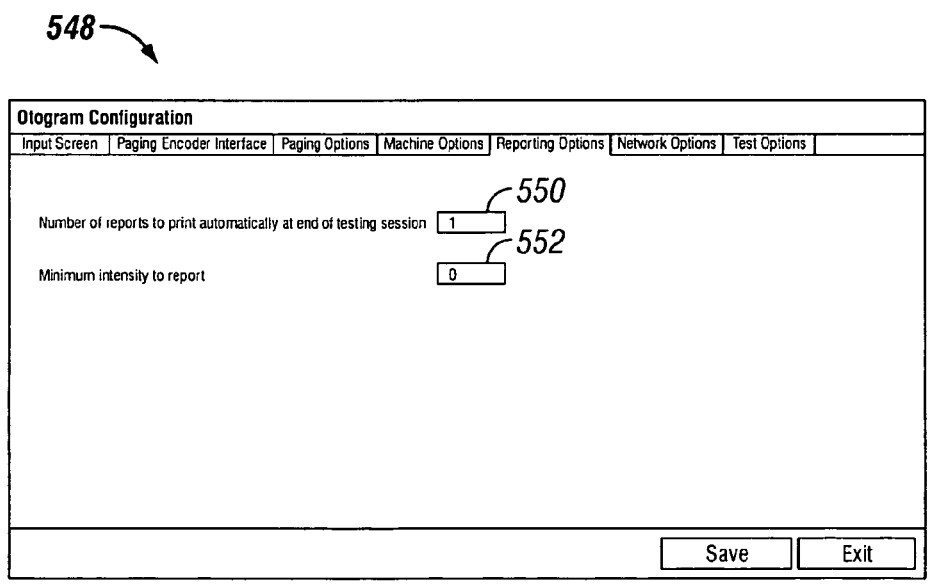

Referring now to FIG. 4, an exemplary implementation of the patient information component 300 is shown. In some embodiments, the patient information component 300 may include a new session screen 400. This is the first screen to be displayed after powering on the system 100 and functions to allow the operator and/or the patient to enter certain items of basic information for the patient. For example, the new session screen 400 may include a chart number field 402 for entering the patient's chart number and a patient name field 404 for entering the patient's name. This information, along with the date and possibly other information, may be used to store and subsequently retrieve the results of any test session. In addition, because the automated hearing test is capable of testing in multiple languages (e.g., English, Spanish, French, etc.), in some embodiments, the new session screen 400 may also include a field 406 for selecting which language to be used to test the patient. The new session screen 400 may also include a plurality of checkboxes 408 for selecting which hearing related tests will be performed for the patient. For example, the new session screen 400 may include a checkbox for selecting a tympanogram test, an acoustic reflex test, and a distortion product (DP) otoacoustic emission test. Also available for selection are an air and bone conduction test, a speech reception test, and a speech discrimination test. Selecting a patient survey allows the automatic hearing test to gather certain hearing related information about the patient that can be used by the hearing health professional to diagnose and recommend treatment.

From the new session screen 400, the operator may access various functions related to the automatic hearing test by pressing the appropriate buttons. For example, pressing a view reports button 410 allows the operator to view patient reports previously stored on the system 100. This aspect of the invention will be described later herein with respect to the reporting component 312. The operator may also press an advanced options button 412 to view and select various advanced options related to a manual testing feature of the automated hearing test. Such annual testing allows the hearing health professional to manually administer the hearing test using various functions of the automated hearing test (i.e., computer-assisted audiometry). An Off button 414 allows the operator to turn the automated hearing test off. Finally, a reconfiguration button 416 allows the operator to initiate the system configuration component 302 of the user interface 208, described below.

FIGS. 5A-5M illustrate an exemplary implementation of the system configuration component 302 of the user interface 208. In some embodiments, the system configuration component 302 includes a plurality of screens, each screen presenting a different set of system configuration options from which the operator may select. It should be noted that not all screens need to be present in every embodiment, and that additional screens not expressly shown may be present in some embodiments.

In one embodiment, the system configuration component 302 may include an input screen 500. The input screen 500 may have an information selection area 502 that allows the operator to select various items of information to be entered for the patient. The information selection area 502 may include fields for the doctor's name, the clinic's name, the patient's date of birth, the patient's gender, and the name of the operator. The information selection area 502 also allows the operator to choose whether to make certain information items optional only, or required information. Thereafter, at the start of each new test session, the new session screen 400 displays all the fields in the information selection area 502 selected by the operator and then waits for the patient and/or the operator to fill in the fields, either on an optional or a required basis.

In some embodiments, the input screen 500 may also include fields for entering default settings for some of the information items. For example, the input screen 500 may include a default doctor's name field 504, a default administrator's name field 506, a default clinic's name field 508, and a default chart number field 510. In some embodiments, the input screen 500 may further include an area for entering several default doctor names into a list 512 and several default administrator names into a list 514. The names that are entered into the lists may then be used as default options in a drop-down list from which the operator and/or the patient may select to fill out the information fields. To add or remove a name from the list, one simply clicks on the appropriate "Add" or "Remove" buttons as needed. To scroll through the list, one simply clicks the "Up" or "Down" navigation buttons as needed.

In some embodiments, the system configuration component 302 further includes a paging encoder interface screen 520. By way of background, the automated hearing test typically includes a patient response system that allows the operator to monitor the patient's progress during the hearing test and also allows patient to contact the operator, usually via a pager, at any time during the test. The function of the paging encoder interface screen 520 is to let the operator customize the paging protocol used by the automated hearing test. To enable paging, for example, a check box 522 may be selected to indicate that a paging device is attached to the automated hearing test. The paging encoder interface screen 520 also makes available a plurality of options 524 for specifying various parameters of the paging encoder interface, such as the communications port, an encoder ID, an encoder timeout period, a pager CapCode, and a pager data rate.

In some embodiments, the system configuration component 302 further includes a paging options screen 530. The paging options screen 530 allows the operator to select when a page will be issued. For example, the paging options screen 530 may include a check box 532 for paging the operator at the end of the test session, a check box 534 for paging the operator at the end of each test in the test session, a check box 536 for paging the operator after a certain amount of inactivity by the patient, and a check box 538 for paging the operator if the automated hearing test cannot determine a pure tone threshold for the patient within a predetermined amount of time.

The paging options screen 530 also includes a plurality of paging options 539 that allows the operator to customize certain aspects of the page. For example, the operator may specify a short text message to be sent with pages that occur at the end of a testing session, and a brief text message to be sent with pages that occur at the end of each test. The operator may also specify a short text message to be sent with pages that occur due to inactivity, and to specify the inactivity threshold. Furthermore, the operator may specify a brief text message to be sent with pages that occur due to the inability to reach a pure tone threshold, and to specify the amount of time to wait for a threshold.

The paging device option 540 allows the operator to specify the type of paging mechanism. For example, the operator may specify a wireless or radio based paging mechanism, a web based paging mechanism wherein an alarm (visual and/or audio) is issued on a web page monitored by the operator, or an FTP based paging mechanism where a file is sent to the operator to notify him of a paging event.

In some embodiments, the system configuration component 302 further includes a machine options screen 544. The function of this screen is to allow the operator to assign a specific identifier to the automated hearing test. This function is especially useful in clinics where multiple systems are used. For example, the machine options screen 544 may include a machine identifier field 546 into which the operator may enter an alphanumeric identifier for the particular automated hearing test.

In some embodiments, the system configuration component 302 further includes a reporting options screen 548. The function of this screen is to allow the operator to pre-configure the number of test reports to be printed automatically after each testing session. For example, the reporting options screen 548 may include a field 550 for entering the number of reports to be printed automatically at the end of a testing session (e.g., 2). In some cases, the reporting options screen 548 also includes a field 552 for entering the minimum testing intensity level that the operator wishes to be reported (e.g., 0 dB).

In some embodiments, the system configuration component 302 further includes a network options screen 554. The function of this screen is to allow the operator to specify where patient reports are stored on a particular computer 102 of the automated hearing test. In the example shown, a field 556 indicates that the patient reports are stored in a directory called "c:\inetpub\wwwroot\" of computer 102. When the computer 102 is accessed from a network, the information that will be available to the network is the patient reports that are stored in the specified directory. Thus, any personnel with authorized access to the network to which the computer 102 is connected may view the patient reports that are stored on the computer 102. In some embodiments, the computer 102 of each automated hearing test functions as a web server, and the field 556 indicates the web server root directory. In that case, the patient reports stored on the computer 102 may be viewed from the network as a web page using any suitable web browser.

In some embodiments, the system configuration component 302 includes a test options screen 560. The function of this screen is to allow the operator to configure various aspects of the hearing related tests that will be performed. For example, the test options screen 560 includes a plurality of checkboxes 562 that allow the operator to specify which hearing related tests will be selected by default from the new sessions screen 400.

The test options screen 560 also includes a plurality of hearing related test option screens, for example, a pure tone options screen 566. Because naming conventions for the various hearing related tests differ from country to country, the pure tone test options screen 566 includes a naming field 568 to allow the operator to customize the test name used for this test in his clinic. The pure tone test options screen 566 further includes frequency options 570 that allow an operator to specify when the various pure tone frequencies are tested. For example, the operator may specify that a certain frequency is always tested, never tested, or tested as needed. The operator may define the pure tone average (PTA) for the pure tone test by selecting one of several predetermined definitions at 572. A check box 574 allows the operator to always use bone masking if he so desires.

In some embodiments, another hearing related test options screen that is included is the tympanometry options screen 576. This tympanometry options screen 576 allows the operator to specify various parameters for the tympanometry test. For example, the tympanometry options screen 576 includes field 578 where the operator may specify a name for the test, the communications port, and may select one of several available to manometer. The tympanometry options screen 576 also includes field 580 for allowing the operator to specify the starting pressure and the ending pressure for the test. A plurality of calibration parameters 582 allows the operator to enter calibration values for the left and right ears and to calibrate the tympanometer for those ears accordingly.

In some embodiments, the test options screen 560 further includes an acoustic reflex options screen 583 that can be used to specify various parameters for the acoustic reflex test. For example, the acoustic reflex options screen 583 may include a field 584 that allows the operator to specify the name to be used with the test. Checkboxes 585 allow the operator to specify which one of several available frequencies to be used with the ipsilateral and contralateral ear. The initial intensity level, incremental intensity, and the reflex threshold level may also be specified in the fields shown at 586.

In some embodiments, yet another hearing related test options screen that is included is the speech discrimination options screen 587. This screen allows the operator to specify various parameters for the speech discrimination test, including the name of the test at 588. A plurality of fields 589 allow the operator to specify, for example, the base presentation level, the presentation type (e.g. closed, open), the number of presentations, the minimum presentation level, the maximum presentation level, and the particular word list to be used.

In some environments, the test options screen 560 additionally includes a speech reception threshold options screen 590 that can be used to specify various parameters for the speech reception threshold test. For example, the speech reception threshold options screen 590 may include a field 591 for specifying the name to be used for the test.

In embodiments where a patient survey is taken, the test options screen 560 may include a survey options screen 592. This screen can be used to specify various aspects of the survey at 593, including the name to be used for the survey, and the particular survey of several available surveys to be used. In some embodiments, the questions that are asked in the survey may comply with the Hearing and Hearing Handicap Inventory for the Elderly (HHIE).

Finally, in some embodiments, the test options screen may include an otoacoustic emission options screen 594. The otoacoustic options screen 594 may include a naming field 595 for specifying the name to be used with this test. A set of options 596 allows the operator to select which one of several frequencies to test, set the response floor and noise ceiling, and specify the intensity levels L1 and L2.

Figure 6A:
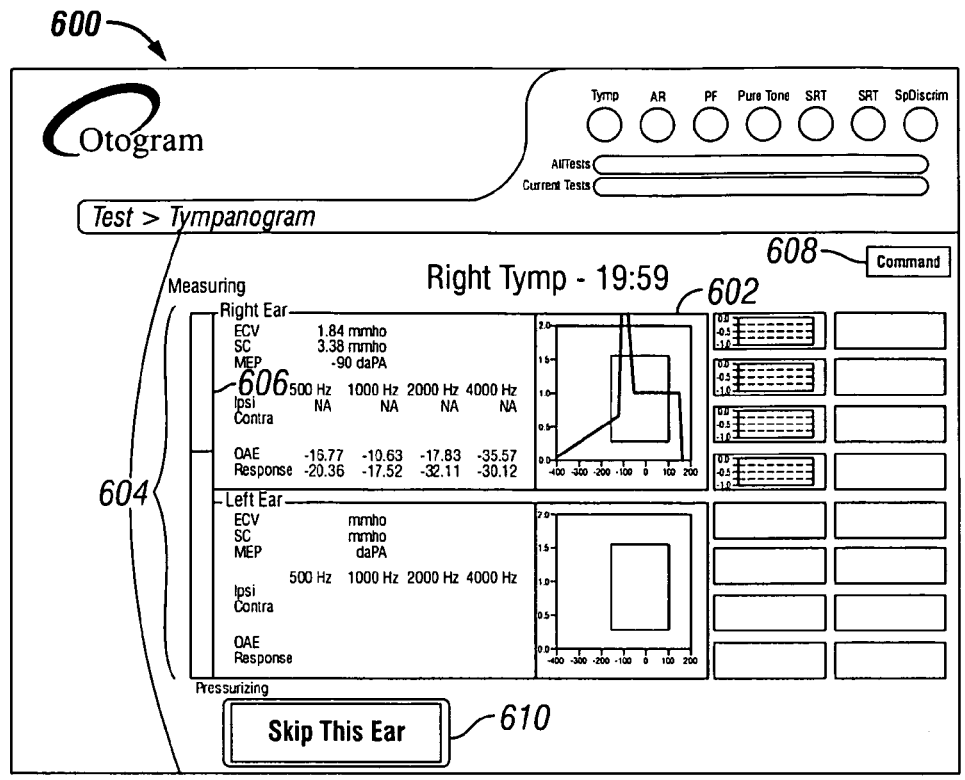
FIGS. 6A-6B illustrate an exemplary implementation of a tympanometry, acoustic reflex, and otoacoustic emission component of the user interface according to embodiments of the invention.
Figure 6B:
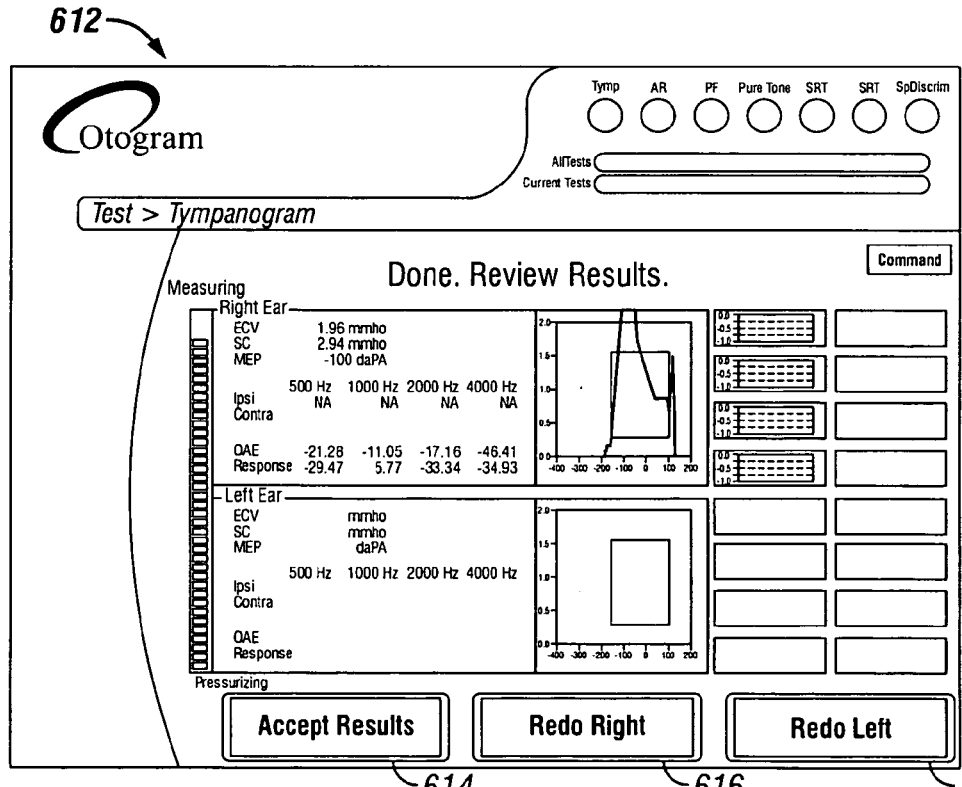

FIGS. 6A-6B illustrate an exemplary implementation of the tympanometry, acoustic reflex, and otoacoustic emission component 304 of the user interface 208. In some embodiments, the tympanogram, acoustic reflex, and otoacoustic emission component 304 includes a combination test screen 600. The function of this screen is to allow the operator and/or the patient to obtain a tympanogram, acoustic reflex, and otoacoustic emission measurement for the patient. Note that although all three tests may be performed from the same screen, only the tests that have been selected will be performed. The tympanogram, acoustic reflex, and otoacoustic emission screen 600 may include a series of instructions for the operator and/or patient that walks him step-by-step through the procedure. The instructions may be presented in text, or they may be presented verbally, or both. Where verbal instructions are presented, a confirmation button (not expressly shown) may be pressed to confirm completion of each instruction and move on to the next instruction. While the test is being performed, the screen 600 may include a chart 602 that captures the data being obtained for the tympanogram. The raw data is shown generally at 604. The amount of pressure that is being used is shown at 606. Pressing a command button 608 brings up a list of commands that may be selected (e.g., exit, pause, microphone on, etc.). Pressing a skip button 610 allows the operator and/or the patient to skip the current ear and move to the next ear.

When the tympanogram, acoustic reflex, and otoacoustic emission portion is completed, a screen 612 presents the final results. From this screen, the operator and/or patient may press an accept results button 614 to accept the results, a redo right ear button 616 to redo the right ear, and a redo left ear button 618 to redo the left ear.

Once the tympanogram, acoustic reflex, and otoacoustic emission portion is completed and the results therefor accepted, the patient may proceed with the remaining hearing related tests. First, however, the patient should be given some instructions and guidance on how to proceed and what to expect. The patient training component 306 performs this training task. Patient training is given in two phases, a general training phase where general instructions are given, and a test specific phase where instructions that are specific to a particular test are given before the test begins.

Figure 7A:
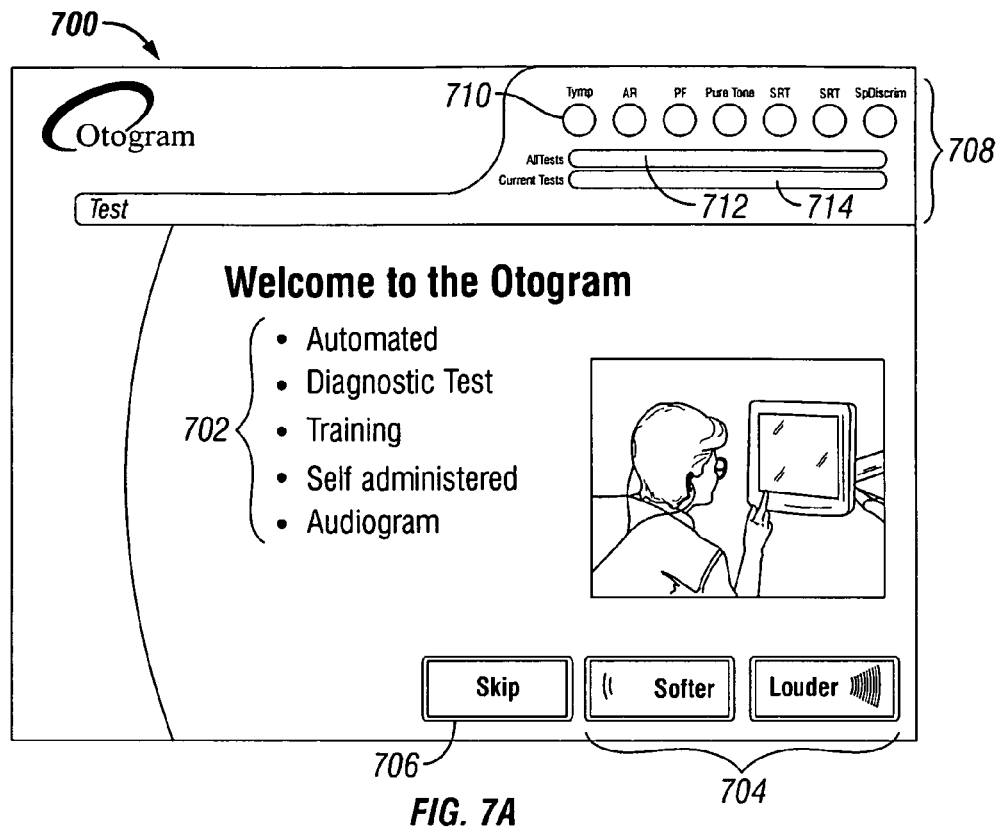
FIGS. 7A-7B illustrate an exemplary implementation of a portion of a patient training component of the user interface according to embodiments of the invention.
Figure 7B:
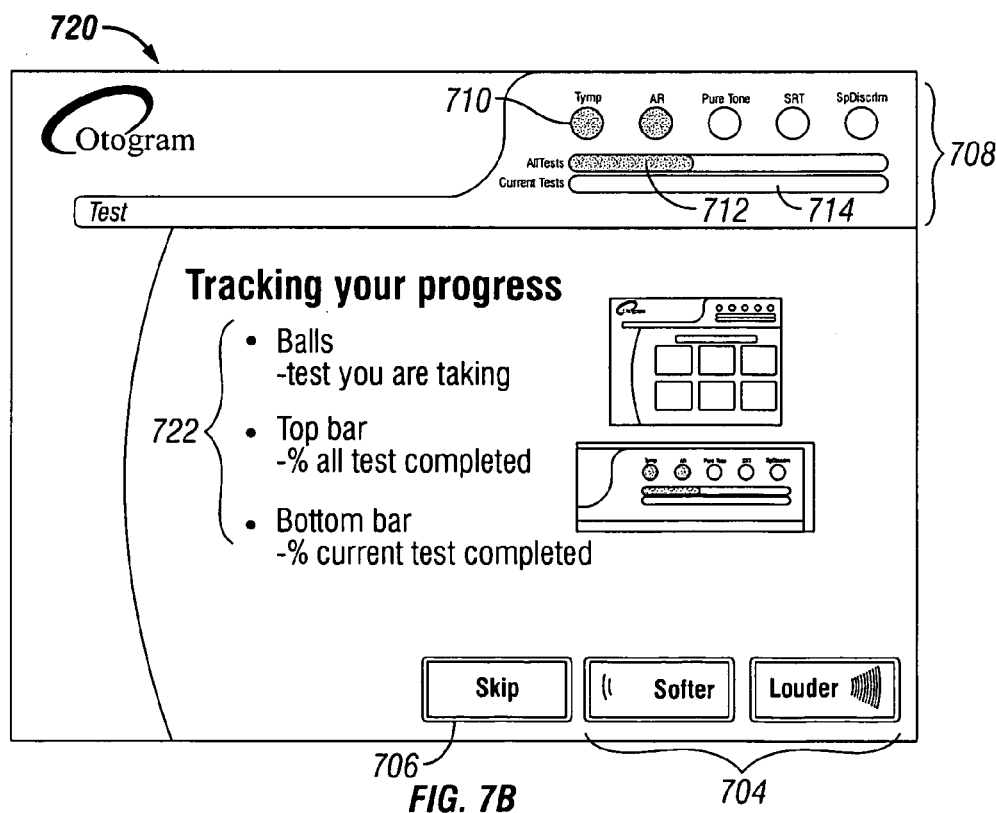
Figure 8A:
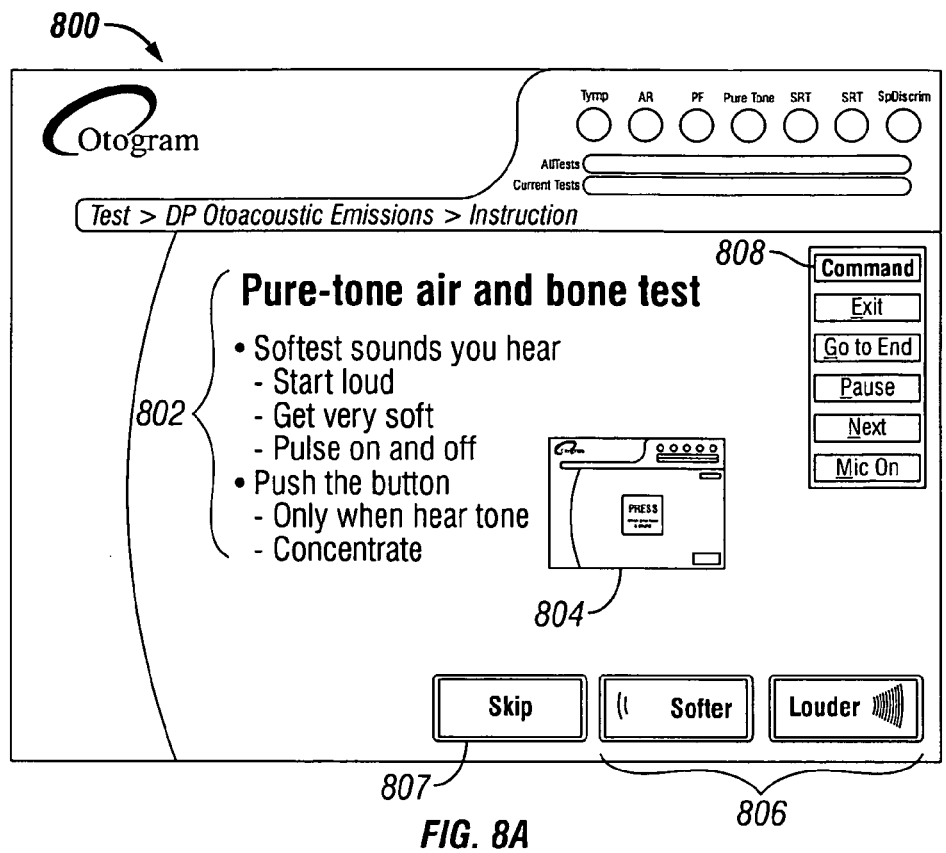
FIGS. 8A-8I illustrate an exemplary implementation of a patient testing component of the user interface according to embodiments of the invention.
Figure 8B:
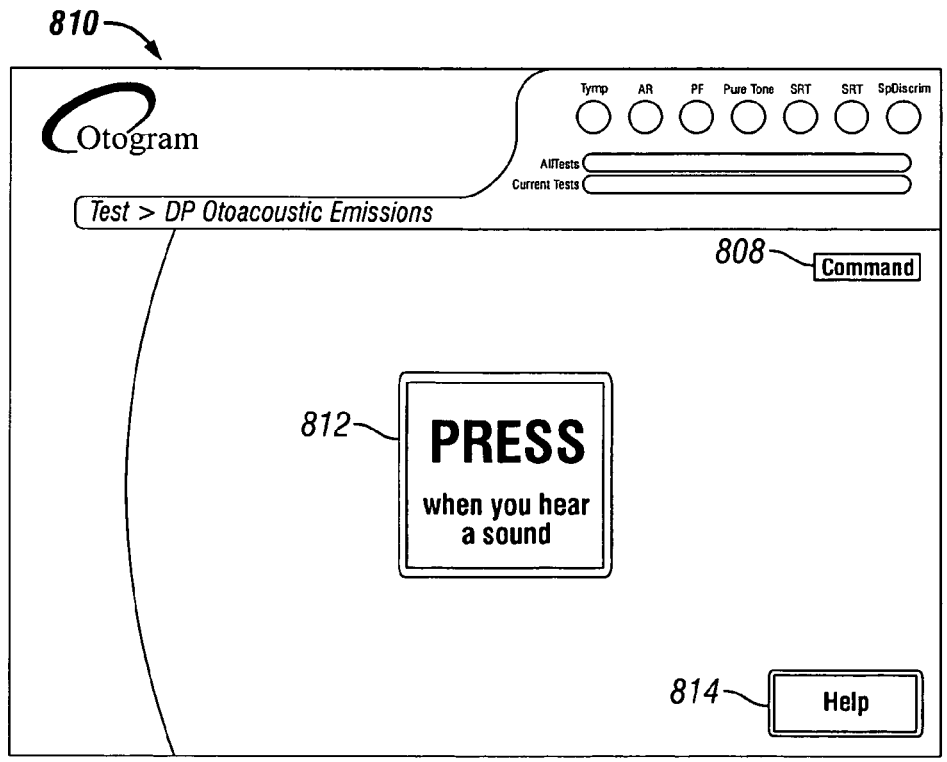
Figure 8C:
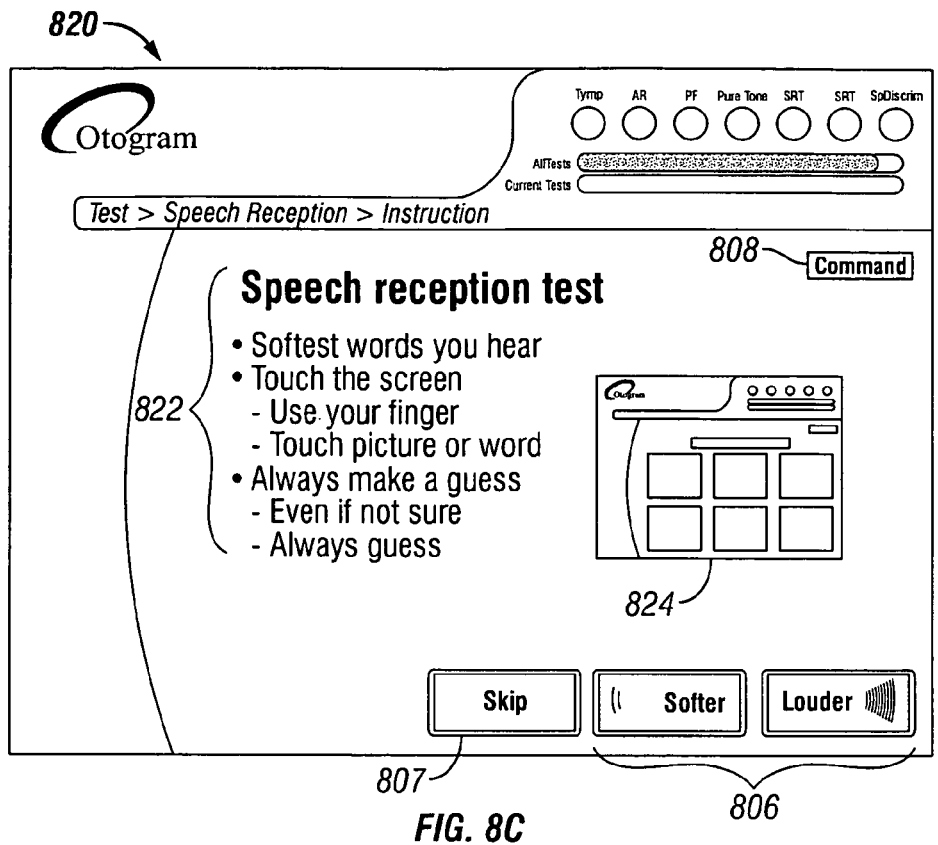
Figure 8D:
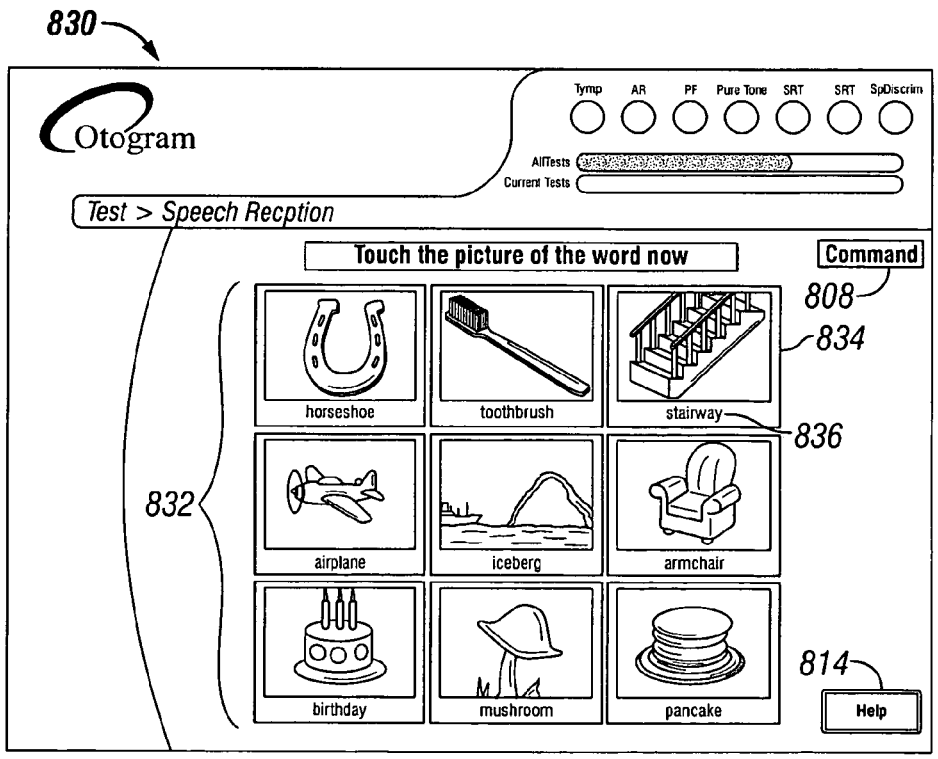
Figure 8E:
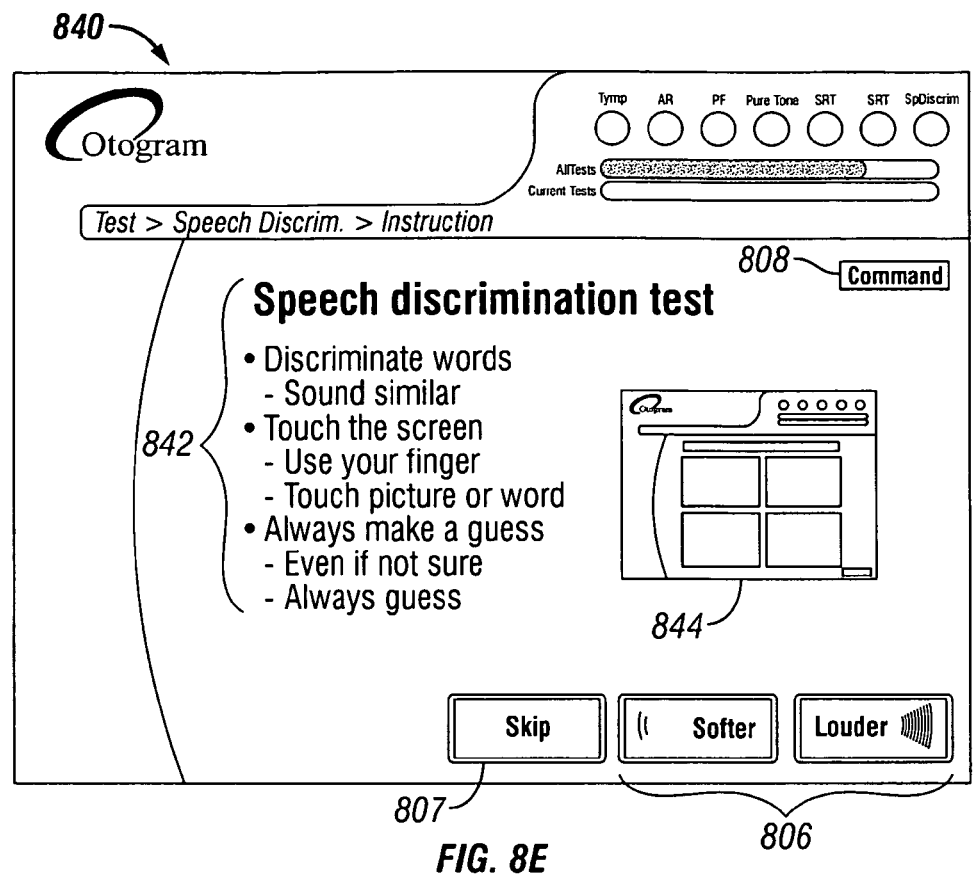
Figure 8F:
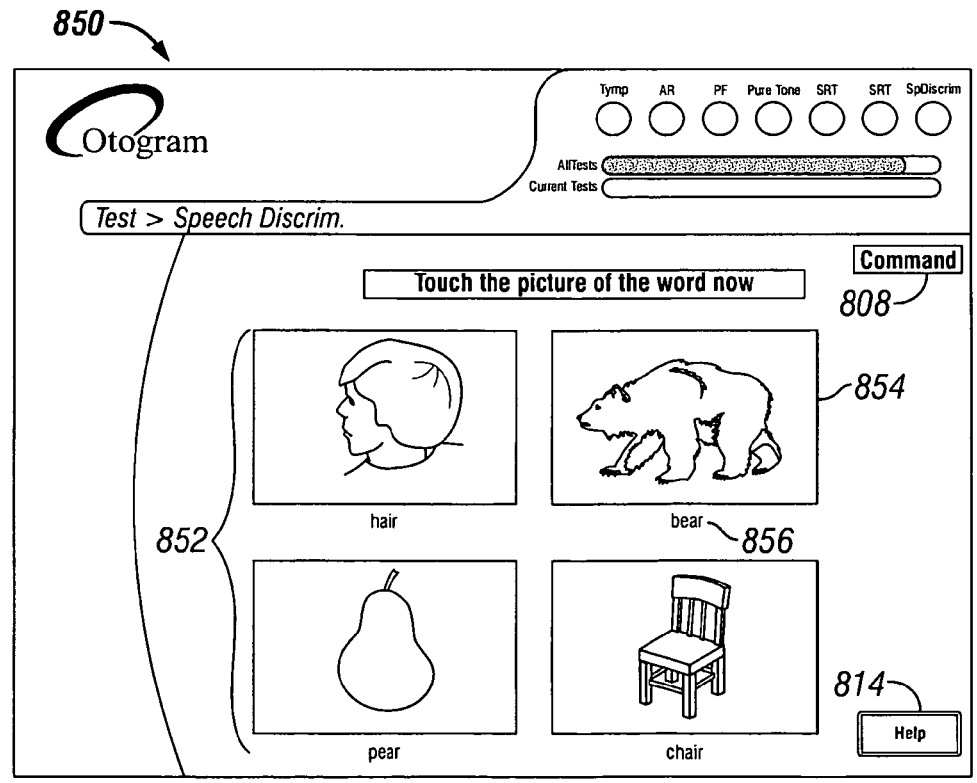
Figure 8G:
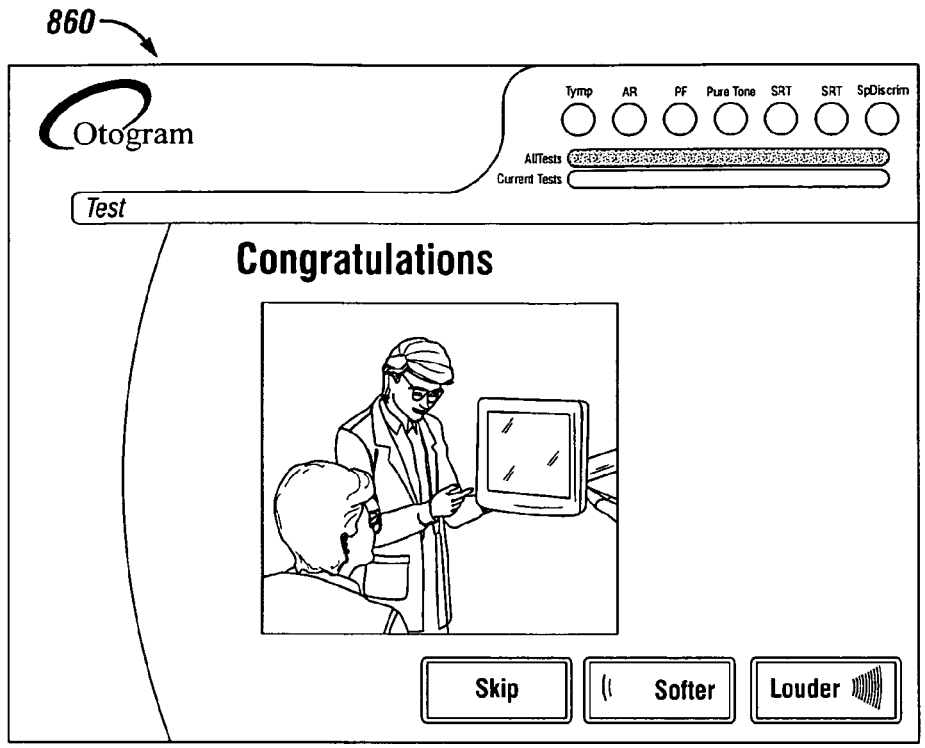
Figure 8H:
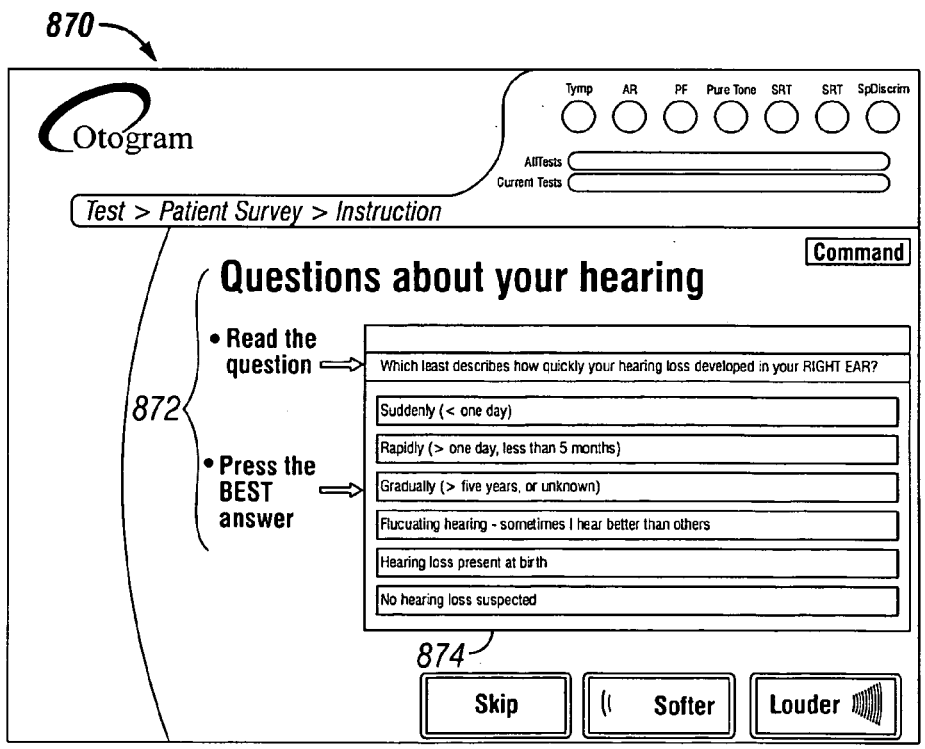
Figure 8I:
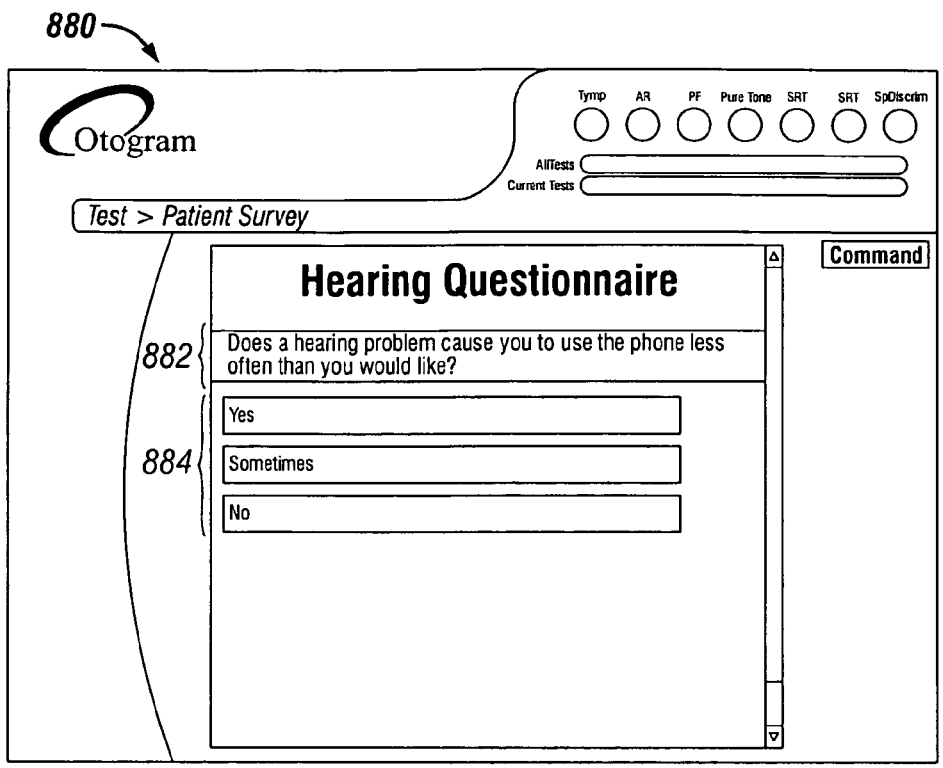

FIGS. 7A-7B illustrate an exemplary implementation of the general phase of the patient training component 306. In some embodiments, the general training phase includes a welcome screen 700. The function of this screen is to give the patient a general idea of how the automated hearing test works in general. For example, the welcome screen 700 may display some of the basic instructions (shown generally at 702) for the automated hearing test. At the same time, the patient training component 306 may cause a verbal welcome message to be played in the transducers worn by the patient. The welcome message may provide the patient with detailed information about the upcoming tests. For example, the welcome message may explain that the tests are automated and therefore the operator may not be in the room during the test, but that the patient may press the help button at any time to call the operator. Volume control buttons 704 allow the patient to increase or decrease the volume of the welcome message as needed. If the patient wishes to skip the message altogether, he may press the skip button 706.

Before discussing the patient training component 306 further, it may be useful to discuss one aspect of the patient management component 310 of the user interface 208. In some embodiments, the patient management component 310 may include a progress indicator 708 that allows the patient and/or operator to track the patient's progress for a given test session. The progress indicator 708 may include a plurality of bubbles, one of which is shown at 710, to indicate the patient's current hearing related test. For example, there may be a bubble for the tympanometry test, the acoustic reflex test, the otoacoustic emission test, the pure tone threshold test, the speech reception test, and the speech discrimination test. The bubbles are empty at first, but as the patient begins a particular hearing related test, the bubble for that test is filled in. The color used to fill in the bubbles may be the same for every bubble, or some type of progressive color scheme may be used (e.g., darker colors at the beginning stages and lighter colors at the end).

In some embodiments, the progress indicator 708 of the patient management component 310 may also include progress bars 712 and 714. The progress bars 712 and 714 provide an indication of the completion percentage of the total test session and of each individual hearing related test, respectively.

Continuing now with the general training phase of the patient training component 306, if a progress indicator 708 is present, the patient training component 306 also provides training on how the patient can track the progress of his testing using the progress indicator 708. For example, after the welcome message is completed (or skipped), the patient training component 306 may present a progress training screen 720. The progress training screen 720 may display a text explanation 722 of the basic feature of the progress indicator 708. In addition, or alternatively, a detailed verbal explanation of the progress indicator 708 may also be presented. Both the text and verbal based training explain to the patient how to interpret the plurality of bubbles 710 and the progress bars 712 and 714.

After the general training stage is completed, the patient training component 306 then provides the test-specific training. The test-specific training may be provided for the specific tests that are about to be performed only, or it may be provided for all the available hearing related tests. In addition, the test specific training may be provided all at once and upfront before beginning any specific test, or the training for a specific test may be provided one test at a time before beginning that hearing related test. This latter embodiment will now be explained in conjunction with an explanation of the patient testing component 308.

In general, at the beginning of each test, the patient training component 306 presents the patient with an instruction screen and/or a verbal explanation of the test. The instruction screen may show some of the basic instructions for the test and how to proceed, and the verbal explanation may provide a more detailed explanation. The patient testing component 308 then allows the patient to proceed with the actual testing. FIGS. 8A-8I illustrate an exemplary implementation of the patient testing component 308 and the test specific training portion of the patient training component 306.

For example, where the patient is getting ready to take the pure tone threshold portion of the automated hearing test, the patient training component 306 presents the patient with a pure tone threshold training screen 800 and, in some cases, a verbal explanation thereof. The pure tone threshold training screen 800 includes text 802 that lists some of the basic instructions for the pure tone threshold test. For example, the text may explain that the tones start loud, then get soft, then pulse on and off. The training screen 800 may also present an example 804 of the response button with an explanation that the patient is to push the button only when he hears a tone. The verbal explanation, when used, may provide essentially the same information plus a few more details, such as the fact that one ear will be tested at a time, and may also provide a sample tone. Volume control buttons 806 allow the patient to control the volume of the verbal message, and a skip button 807 allows the patient to skip the verbal message. A command button 808 brings up a list of commands that may be used at this point.

After the pure tone threshold training is completed, the patient testing component 308 presents the patient with a response screen 810 for responding to the pure tone threshold test. The purpose of the pure tone threshold test is to determine the patient's hearing threshold (i.e., the softest level he can hear) at various frequencies or tones. To this end, the response screen 810 may include a button 812 that the patient can press each time he hears a tone. Where color is used, the button 812 and the screen 810 may have a comfortable yet distinctive color scheme that helps the patient to concentrate on the test. For example, the button may be vivid color such as red, while the surrounding area may have a lighter, softer color. Other suitable color schemes may also be used here as well as throughout the various drawings. In addition, or alternatively, the patient testing component 308 may activate or engage a separate response button (not expressly shown) that the patient may press each time he hears a tone. The automated hearing test then presents a series of tones to the patient, and the patient testing component 308 waits for the patient to respond by pressing the button 812. A help button 814 allows the patient to call the operator at any time.

Where the patient is to undergo a speech reception threshold portion of the automated hearing test, the patient training component 306 presents the patient with a speech reception training screen 820 and, in some cases, a verbal explanation thereof. The speech reception training screen 820 includes some of the basic instructions 822 for the test, for example, that there will be X pictures, and that the patient should always make a guess at the correct answer, even if he is not sure. In addition, the speech reception training screen 820 may also include an example 824 of the test screen displayed during the test. The verbal explanation, when used, may provide essentially the same information plus a few more details, such as how many pictures will be shown to the patient.

After the speech reception training is completed, the patient testing component 308 presents the patient with a response screen 830 for responding to the speech reception threshold portion of the automated hearing test. The speech reception threshold test is used to determine the softest level at which the patient can hear and recognize a word. To this end, the response screen 830 presents a set 832 of randomly chosen pictures (one shown at 834) to the patient along with the corresponding words (one shown at 836) for the pictures.

In some embodiments, there are nine randomly chosen pictures and words in a set 832, and the same set 832 is used for the entire speech reception threshold portion (although it is possible to use more than one set). Preferably, the words that are used are compound words with two distinct syllables. For languages where no such words are available, appropriate substitutions may be made. The automated hearing test then verbally presents the words to the patient one at a time, randomly, and at a decreasing intensity level, with no emphasis on any syllable. The patient testing component 308 then waits for the patient to select the picture or word from the response screen 830 that matches the verbally presented word. This procedure is performed for each ear until the lowest or softest verbal presentation level at which the patient can correctly identify 50% of words is determined.

Where the patient is to undergo the speech discrimination portion of the automated hearing test, the patient training component 306 presents the patient with a speech discrimination training screen 840 and, in some cases, a verbal explanation thereof. The speech discrimination training screen 840 includes some of the basic instructions 842 for the test, for example, that there will be X pictures, and that the patient should always make a guess at the correct answer, even if he is not sure. In addition, the speech discrimination training screen 840 may also include an example 844 of the test screen displayed during the test. The verbal explanation, when used, may provide essentially the same information plus a few more details, such as how many pictures will be shown to the patient.

After the speech discrimination training is completed, the patient testing component 308 presents the patient with a response screen 850 for responding to the speech discrimination portion of the automated test. The speech discrimination test, unlike the pure tone threshold and speech reception threshold tests, does not test for the softest level the patient can hear. Rather, the speech discrimination test checks to see how well the patient is able to discern between similar sounding words. To this end, the response screen 850 presents randomly chosen sets 852 of pictures (one shown at 854) along with their corresponding words (one shown at 856). The words 856 are preferably single syllable words that sound alike. In some embodiments, there are four such words 856 along with their corresponding pictures 854 in each set 852. For languages where such words are not available, appropriate adjustments may be made.

As each set 852 of pictures is presented on the response screen 850, the automated hearing test verbally presents one of the words 856 to the patient, preferably at a constant level. The level at which the word is verbally presented is chosen so that the patient is mostly like to correctly hear the word presented. Usually the same word from each set 852 is verbally presented. It is possible for some sets 852 to have overlapping pictures, but the same exact set 852 of pictures should not be repeated. The automated hearing test randomly chooses the sets 852 of pictures from a large pool of such sets, then presents one word from each set at a constant level. The patient testing component 308 thereafter waits for the patient to select the picture or word from the response screen 850 that matches the verbally presented word. The automated hearing test continues this procedure until either a sufficient percentage of correct responses has been received (e.g., 85 percent), or a large enough sample has been obtained to give an accurate assessment.

In some embodiments, the patient management component 310 includes a congratulatory screen 860 that is used to notify the patient and congratulate him for successfully completing the hearing related tests. In some cases, the congratulatory screen 860 may also be accompanied by a verbal congratulatory message informing the patient that he has completed the tests and, if appropriate, the patient will now be given instructions for a survey.

An example of a survey instructions screen is shown at 870. The purpose of the survey instructions screen 870 is to instruct the patient regarding how to take the survey. Thus, the survey instruction screen 870 may include a set of instructions 872 that tell the patient, for example, that he should read the questions and then select the best answer. An example of the survey is given at 874. In some embodiments, a verbal message may also be presented that explains the survey in more detail. For example, the verbal message may explain that the purpose of the survey is to gather information about the patient to help the hearing health professional provide a diagnosis and recommend treatment, if necessary.

Once the instructions are completed, the patient is presented with a survey screen 880. The survey screen includes a survey question 882 followed by a set of answers 884. After the patient reads the question, he may then select the best answer from the set of answers 884. This process is continued until all the survey questions have been answered.

Figure 9:
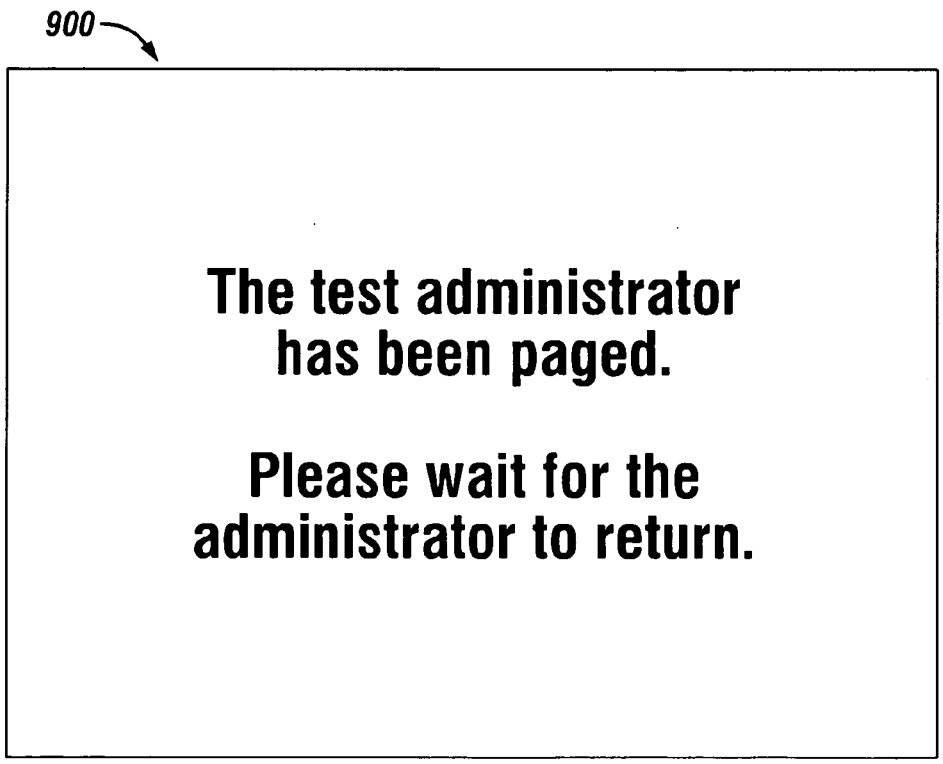
FIG. 9 illustrates an exemplary implementation of a patient management component of the user interface according to embodiments of the invention.

FIG. 9 illustrates an exemplary implementation of the patient management component 310. As mentioned above, the function of the patient management component 310 is to notify the operator and/or patient of any problems or contingencies that may have arisen, and to generally help the patient stay on course through the testing. For example, if the patient is not responding during a test, or is responding too quickly, the patient management component 310 may issue an on-screen warning to the patient. The warning may include a short text message describing the problem to the patient, and may include an on-screen acknowledgment such as an "Okay" button or a "Continue" button. The patient must then acknowledge the warning by pressing the acknowledgement button in order to continue testing. A verbal warning may also accompany the on-screen warning.

If the patient's responses indicate that there is an equipment problem or some other problem that requires the operator's attention, the automated hearing test may alert the operator. Alerting the operator may be accomplished by wireless paging or by any other suitable techniques (e.g., e-mail, console lights, buzzer, etc.). In the event that the operator needs to be paged, the patient management component 310 may include a paging screen 900 that can be used to inform the patient that the operator is being paged. For example, the paging screen 900 may include a short text message saying that the operator is being paged and that the patient should simply wait for the operator to come in.

FIGS. 10A-10F illustrate an exemplary implementation of the reporting component 312 of the user interface 208. The reporting component 312 allows the operator to view the results of the hearing test, and to save them in various formats (e.g., xml, html, etc.). In some embodiments, the reporting component 312 includes a reporting screen 1000 from which the operator may select a number of options. For example, the operator may press the redo some tests button 1002 to redo one or more hearing related tests. Selecting this button returns the operator to the new session screen 400, but the patient's basic information is retained so that one or more tests may be performed again without re-entering the basic information. Pressing the new session button 1004 returns the operator to the new session screen 400, but clears the basic information fields so that new information may be entered.

Pressing the view reports button 1006 allows the operator to search and view the results of previous hearing tests saved on the system 100. Pressing the print billing button 1008 prints the billing information associated with the patient, including insurance codes for services rendered. Pressing the print report button 1010 prints a full report that contains all the relevant results of the patient's hearing test that a physician usually would like to see.

An exemplary report that may be generated when the view report 1006 button is pressed can be seen from the report screen 1020. The report screen 1020 may present the results of the hearing test in a two-panel format, with the results of the right ear in one chart 1022, and the results of the left ear in another chart 1024. Note that only a portion of the results can be seen here, and that the entire report may be viewed by scrolling down the screen as needed. The charts 1022 and 1024 are computer-generated audiograms that reflect the patient's performance for a particular test (e.g., the air and bone conduction test). Other charts are available for other tests within a specific test session, as well as charts from multiple test sessions for a particular patient. The relevant data for each chart is also displayed (generally at 1026), as well as some basic information (generally at 1028), including the patient's name, date and time of the test, chart number, the physician, the tester, the clinic, and the elapsed time for the test.

A save report button 1030 allows the operator to save the results of the current hearing test. Pressing this button brings up a save report dialog box (not expressly shown) that allows the operator to specify a name for the report and to save the report under that name.

A change report style button 1032 allows the operator to change the style of the report from the two-panel format to, for example, a one-panel format 1040, where data for both ears are presented in one chart. As can be seen, the one-panel format 1040 includes a single chart 1042 along with the data therefor (generally at 1044). Basic information 1046 about the patient is also provided. Navigation buttons 1048 allows the operator to navigate around the report.

A view saved report button 1034 allows the operator to view reports that have been previously saved. Note that this task can also be performed by pressing the view reports button 410 from the new sessions screen 400 in FIG. 4. Pressing either button brings up a search screen 1050, from which the operator may search for previously saved reports to open and view. The search screen 1050 includes a plurality of search criteria 1052 that the operator can use to find previously saved reports. Pressing the search button initiates the search. Pressing the display all button 1054 displays all of the previously saved reports.

The reporting component 312 also includes a search result screen 1060 that presents the results of the search. This screen lists all the available reports 1062 that match the one or more search parameters from the report search dialog box 1050. The reports are listed in this example according to the date they were taken, but they may certainly be listed in some other order if desired. In addition to the date information, other information about the reports may also be shown, such as the patient name, the chart number, the test time, the clinic, the physician overseeing the test, and the operator administering the test. In some embodiments, each patient's name and chart number is a hyperlink 1064 that takes the operator to the report associated with that patient's name or chart number. As mentioned previously, in some embodiments, each report can be viewed as a web page using any suitable web browser.

The result screen also includes a log hyperlink 1066 that allows the operator to view a log for any report. The log includes a listing of every action taken by the patient and/or operator (e.g., picked the wrong picture for a word) during the test as well as every action taken by the automated hearing test (e.g., increased intensity at 5 kHz by one increment). A data hyperlink 1068 to the data allows the operator to view the raw data for any test session. A tympanogram hyperlink 1070 allows the operator to view the tympanogram, acoustic reflex, and otoacoustic reflex results. And an audiogram hyperlink 1072 to the audiogram allows the operator to view the audiogram (e.g., chart 1022) by itself without the rest of the report.

Other aspects of the search result screen 1060 may include a plurality of checkboxes (shown generally at 1074), each checkbox corresponding to one of the reports listed, that allows the operator to select several reports. A compare button 1076 allows the operator to view a comparison of the reports that have been selected. Pressing this button brings up a compare screen 1080 that includes a comparison of the data charts from the selected reports, shown at 1082 and 1084, for the right and left ears of the patient. The charts 1082 and 1084 are computer-generated charts that show a comparison of the patient's performance for a particular test (e.g., the air and bone conduction test). Similar comparisons may also be performed for other hearing related tests as well. In some embodiments, for the reports being compared, the older results will be displayed less prominently, and the newer results will be displayed more prominently. A comparison of the relevant data for the charts is also displayed (generally at 1086 and 1088), as well as some basic information (generally at 1090), including the patient's name, dates and times of the test, chart numbers, the physician, the tester, the clinic, and the elapsed time for the more recent test. A navigation button 1096 allows the operator to return to the previous screen.

Figure 11A:
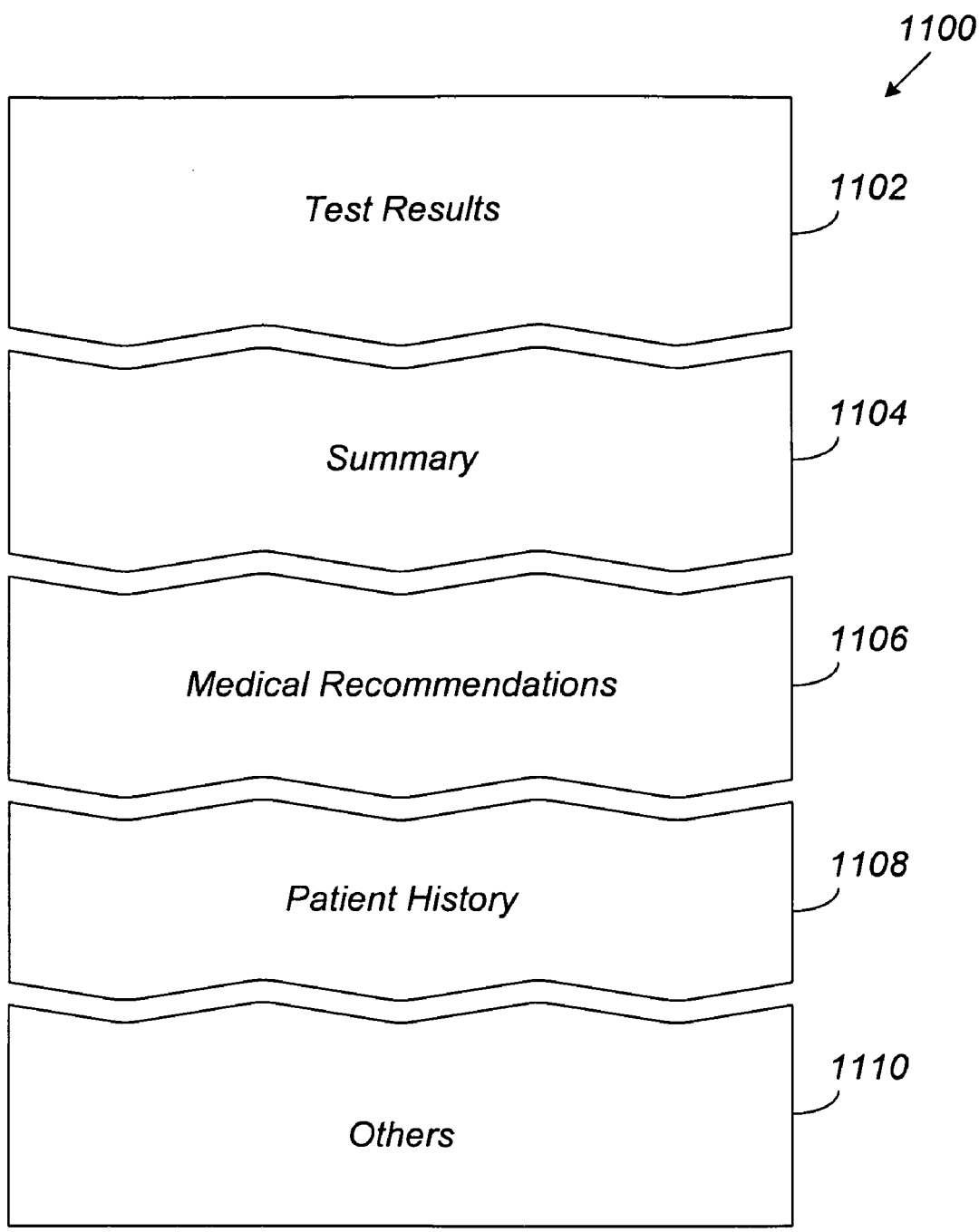
Figure 11B:
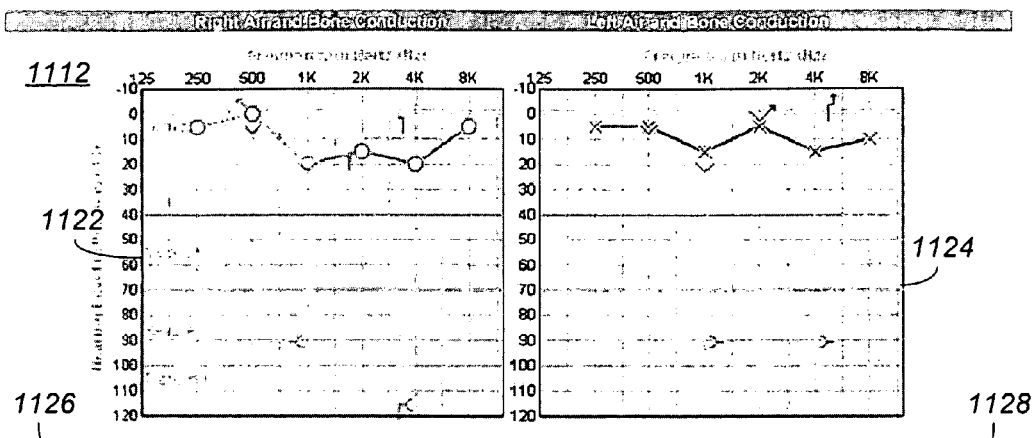
Figure 11B:
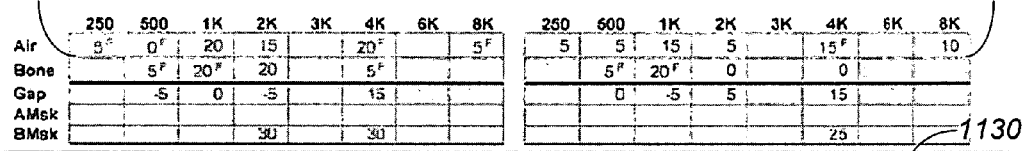
Figure 11B:
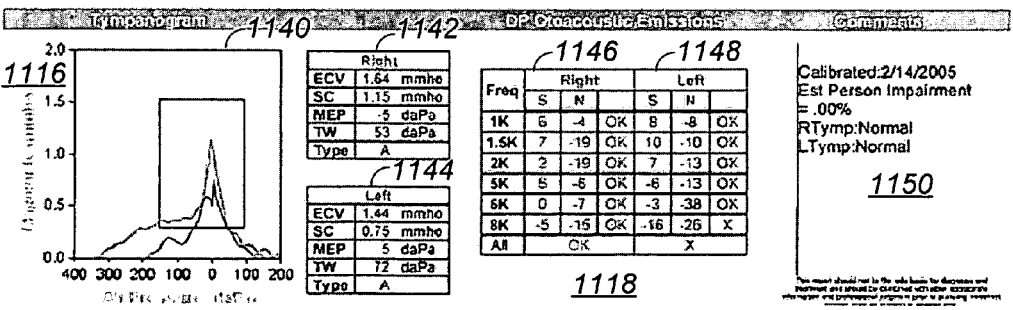

As mentioned above, pressing the print report button 1010 prints a full report that contains all the relevant results of the patient's hearing test. FIGS. 11A-11C illustrate an exemplary hearing test report 1100 according to embodiments of the invention. As can be seen in FIG. 11A, the report 1100 may have several sections, including a test results section 1102, a test summary section 1104, a medical recommendations section 1106, a patient history section 1108, and possibly one or more other sections 1110 (e.g., medical release, billing, etc.). These various sections 1102-1110 together provide a single report that is concise, convenient, and thorough. Note that some of these sections, for example, the test results section 1102, were discussed briefly above with respect to the reporting component 312.

In accordance with embodiments of the invention, one or more of the sections 1102-1110 may include interpretive comments regarding the results of the hearing related tests in the report 1100. The interpretive comments are generated by the interpretive comments component 314 (FIG. 3) of the user interface 208. As alluded to above, the interpretive comments component 314 may be a modular, stand-alone component that is capable of accepting data from and passing data to other functional components. The interpretive comments component 314 generates the interpretive comments based on the same data received by the results reporting component 312. This modularized approach allows the interpretive comments component 314 to function independently of other functional components such that it may be removed from the user interface 208 and/or inserted into another user interface (not expressly shown) with little or no modification. The interpretive comments provide a sort of guide through the test results for the audiologist or other hearing health professional, noting potential inconsistencies, asymmetries, and areas of concern in the test results and, where appropriate, may recommend certain types of medical treatment in some instances. In no instances, however, are the interpretive comments intended to replace the judgment or medical evaluation of the audiologist or hearing health professional.

For the pure tone frequency threshold tests, the interpretive comments provide information about the degree and the type of hearing loss. The degree of hearing loss refers to the severity of the loss and may be characterized as "normal," "mild," "moderate," "severe," or "profound." These characterizations are based on accepted audiology standards and are dictated by the range where the patient's results fall, but it is also possible to customize the characterizations if desired. The types of hearing loss may range from "normal," "mixed," and "unspecified" to other types of hearing loss. An exemplary list of hearing loss types is provided below in Table 1 along with a brief description of each. In Table 1, the term "SNHL" refers to sensorineural hearing loss.

TABLE 1

| Type | Description |
| --- | --- |
| Normal | No hearing loss detected. |
| Essentially normal | All values except one fall within the normal range or all pure tones are within normal limits with a mild air-bone gap noted. |
| SNHL | Hearing loss detected with no air-bone gaps greater than 10 dB noted. |
| Predominately SNHL | Hearing loss detected with minimal air-bone gaps and normal tympanogram (if data available). |
| Conductive | Hearing loss detected with significant air-bone gaps noted and bone thresholds less than 25 dB. |
| Mixed | Hearing loss detected with air-bone gaps noted and at least one bone threshold greater than 20 dB. |
| Unspecified | Hearing loss cannot be classified because bone conduction scores do not clearly define the type of hearing loss (e.g., SNHL, conductive, mixed, etc.). |
| Inconsistent/ Incomplete data | Test results do not fall within software guidelines and are unable to be interpreted. |

To arrive at the appropriate type of hearing loss for the pure tone frequency threshold test, the interpretive comments component applies the test results to a set of rules that are based on the gap between the air conduction threshold and the bone conduction threshold. Table 2 below provides an exemplary list of the air-bone gap rules that may be used to derive the type of hearing loss for the pure tone frequency test. These rules are intended to be examples only and a different set of rules may certainly be used depending on the particular application. In Table 2, the term "limit" refers to the audiology equipment limit (i.e., the audiology equipment has reached its maximum capability) and the tympanometry type refers to industry accepted tympanometry classifications.

TABLE 2

| Rule | Condition |
| --- | --- |
| 1 | All gaps are less than or equal to 10 dB AND the number of gaps that are less than −10 dB is less than two AND all other gaps are −10 dB. |
| 2 | The gap at 500 Hz is less than 10 dB AND the gaps at 1 KHz, 2 KHz, and 4 KHz are less than or equal to 10 dB AND the number of gaps less than −10 dB is less than two AND all other gaps are greater than −10 dB. |
| 2.1 | The gap at 500 Hz is equal to 15 dB AND the gaps at 1 KHz, 2 KHz, and 4 KHz are less than or equal to 10 dB and the tympanometry is Type A and the number of gaps less than −10 dB is less than two AND all other gaps are greater than −10 dB. |
| 3 | The gaps at 500 Hz and 1 KHz are greater than 10 dB AND are not at the limit AND the number of gaps greater than −10 dB is greater than two AND all other gaps are less than −10 dB; OR the gaps at 1 KHz and 2 KHz are less than 10 dB AND are not at the limit AND the number of gaps greater than −10 dB is greater than two AND all other gaps are less than −10 dB; OR the gaps at 2 KHz and 4 KHz are less than 10 dB AND are not at the limit AND the number of gaps greater than −10 dB is greater than two AND all other gaps are less than −10 dB. |
| 3.1 | The gaps at 2 KHz and 4 KHz are greater than 10 dB AND are both at the limit AND the tympanometry is Type A (if no tympanometry data is available, then the gap at 500 Hz and 1 KHz must be less than 15 dB); OR the gap at 4 KHz is greater than 10 dB AND at the limit AND the tympanometry is Type A (if no tympanometry data is available, then the gaps at 500 Hz and 1 KHz must be less than 15 dB). |
| 4 | The gap at 1 KHz is greater than 10 dB AND the number of gaps less than −10 dB is less than two AND all other gaps are greater than −10 dB; OR the gap at 2 KHz is greater than 10 dB AND the number of gaps less than −10 dB is less than two AND all other gaps are greater than −10 dB; OR the gap at 4 KHz is greater than 10 dB AND the number of gaps less than −10 dB is less than two AND all other gaps are greater than −10 dB AND the gap at 500 Hz is less than 15 dB. |
| 5 | The gaps at 500 Hz, 1 KHz, 2 KHz, 4 KHz are greater than 10 dB AND are not at the limit AND the number of gaps less than −10 dB is less than two AND all other gaps are greater than −10 dB; OR the gaps at 500 Hz, 1 KHz, 2 KHz are greater than 10 dB AND are not at the limit AND the number of gaps less than −10 dB is less than two AND all other gaps are greater than −10 dB; OR the gaps at 1 KHz, 2 KHz, and 4 KHz are greater than 10 dB AND are not at the limit AND the number of gaps less than −10 dB is less than two AND all other gaps are greater than −10 dB. |
| 6 | All bone scores are at the limit and the tympanometry is Type A. |

Using the above set of air-bone gap rules, the interpretive comments component is able to determine the hearing loss type for the pure tone frequency threshold test. The interpretive comments component can determine the hearing loss type if certain air-bone gap rules are true along with certain conditions. An exemplary combination of rules and conditions required for each hearing loss type is shown in Table 3. In Table 3, references to "Rule" refer to the rules listed in Table 2 above and "#1," "#2," and "#3" indicate different circumstances under which the hearing loss type may occur.

For the Distortion Product-Otoacoustic Emissions (DP-OAE) test, the interpretive comments indicate whether the individual scores pass or fail and whether the overall results pass or fail for each ear.

Interpretive comments are also available for the speech discrimination test. The speech discrimination test score is calculated by subtracting the actual speech discrimination score from the predicted speech discrimination score. Based on these speech discrimination loss score, the interpretive comments may include, for example, "Normal" if the dis-

TABLE 3

| Type | Condition |
| --- | --- |
| Normal | All air thresholds less are than or equal to 20 dB; AND All bone thresholds are less than or equal to 20 dB; AND Rule #1 is true. |
| Essentially normal #1 | No air thresholds are greater than 30 dB; AND One air threshold is greater than 20 dB; AND Rule #1 is true or Rule #4 is true. |
| Essentially normal #2 | All bone thresholds are less than 25 dB; AND Rule #2.1 is true or Rule #4 is true; AND All air thresholds are less than 25 dB. |
| Essentially normal #3 | Air threshold for 8 KHz is greater than 20 dB; AND All other air thresholds are less than 25 dB; AND Rule #1 is true. |
| Predominately SNHL | Two or more thresholds are greater than 20 dB; AND Rule #4 or Rule #3.1 is true. |
| Predominately SNHL ("severe" to "profound" degrees of hearing loss) | All air scores are greater than bone scores; AND Rule #6 is true. |
| SNHL | Two or more thresholds greater than 20 dB; Rule #1 is true. |
| Conductive | All bone thresholds less than or equal to 20 dB; AND Rule #2 or Rule #3 or Rule #5 is true. |
| Conductive (Predominately SNHL) | All bone threshold less than or equal to 20 dB; AND Rule #2.1 true; AND Two or more air thresholds greater than 20 dB. |
| Mixed | Two air thresholds greater than 20 dB; AND One or more bone threshold greater than 20 dB; AND Rule #2 or Rule #3 or Rule #5 is true. |
| Mixed (Predominately SNHL) | Two air thresholds greater than 20 dB; AND One or more bone threshold greater than 20 dB; AND Rule #2.1 is true. |
| Unclassified #1 | Two or more air thresholds greater than 20 dB; AND No bone conduction scores. (Label as "predominately SNHL as indicated by air conduction and the tympanometry/acoustic reflex results" if the tympanometry is Type A and one or more ipsi reflexes are present. |
| Unclassified #2 | Two or more air thresholds greater than 20 dB; AND All gap rules are false. (Label as "predominately SNHL as indicated by air conduction and the tympanometry/acoustic reflex results" if the tympanometry is Type A and one or more ipsi reflexes are present. |
| All other circumstances | Label as "insufficient/inconsistent data." |

Interpretive comments may also be generated for the speech reception threshold (SRT) test. For this test, the interpretive comments note the correlation of the SRT and predicted SRT for each ear to alert the audiologist or other hearing health professional to any potentially poor quality tests. Thus, possible interpretive comments for the SRT test include: "consistent" if the SRT scores are within 10 dB of each other; "marginally consistent" if the SRT scores are within 20 dB of each other, and "inconsistent" if the SRT scores have a greater than 20 dB difference. A comment of "marginally consistent" or "inconsistent" on the SRT score means that the audiologist or hearing health professional should reconsider the validity of the test results. This may occur if a patient is malingering or is unable to provide reliable responses for the SRT and/or the pure tone test.

crimination loss is between 0-19% and "Unexpected Loss" if the discrimination loss is 20% or greater. A loss of 20% or higher is considered to be a pathological indication.

In some embodiments, interpretive comments may also indicate asymmetries. Comments denoting asymmetries are presented, for example, if a significant difference is found for the pure tone threshold test. Since this test compares the right and left ear pure tone air conduction scores at each frequency, it is susceptible to asymmetrical results. Thus, if there is more than a 15 dB difference between the two ears at a given frequency, an asymmetrical comment is noted and the frequency listed accordingly. An asymmetrical comment may also be noted to indicate that the SRT scores show a difference of 20 dB or more between the two ears. Finally, an asymmetrical comment may be noted to indicate that the speech discrimination scores show a greater than 20% difference between the two ears.

As mentioned above, in some embodiments, the report 1100 may also suggest medical recommendations based on the test results. The medical recommendations are generated by the interpretive comments component and may include several types of recommendations: medical referral/treatment, amplification, hearing conservation, re-testing, and the like. These recommendations are typically accompanied by a comprehensive case history and medical examination in order to determine the most appropriate next steps. Of course, fewer or additional types of recommendations may also be presented depending on the application without departing from the scope of the invention.

Exemplary recommendations for medical referral/treatment include, for example, "Likely" and "Unlikely." "Likely" is used if the results show mixed or conductive hearing loss. The "Likely" recommendation may also be triggered by asymmetrical pure tones thresholds for two or more frequencies, discrimination loss of 20% or more in either ear, or conductive or mixed hearing loss with significant air-bone gaps in either ear that are corroborated by tympanometry results (if data is available). Since all of these results are suggestive of other medical problems that may require medical treatment or evaluation, the interpretive comments recommend that the patient is referred for treatment. "Unlikely" is used if no asymmetries, significant air-bone gaps or speech discrimination loss is reported. A recommendation of "Possible-unspecified loss, retest/referral may be needed" is presented if the hearing loss type is determined to be "unspecified" (which may be due to the absence of bone conduction results).

Amplification recommendations are based on the average of the two worst pure tone frequencies from 500 Hz to 4 KHz. Examples of recommendations for amplification include: "None" if the average is less than 35 dB; "Recommended" if the average is 35 dB or greater, the hearing loss is sensorineural, and the medical referral/treatment recommendation is "Unlikely"; "Reassess after medical referral/treatment" if the average of the two worst pure tone thresholds between 500 Hz and 4 KHz is 35 dB or greater and the medical referral/treatment recommendation is "Likely." The "Reassess after medical referral/treatment" comment indicates that one of the following was reported on the results: conductive or mixed hearing loss, speech discrimination loss, or significant asymmetry for the pure tone thresholds.

Exemplary recommendations for conservation/hearing protection typically include "recommended" in order to urge the patient to always be protective of his hearing. Exemplary recommendations for retest typically include "1 year" or "as needed" in order to encourage the patient to obtain regular follow-ups.

The foregoing interpretive comments may be displayed on the report 1100 in one or more of the sections 1102-1110, as will now be described with respect to FIGS. 11B and 11C. Turning first to FIG. 11B, the results section 1102 may have several subsections, with the number of subsections depending on the number of hearing tests conducted on the patient. In the example shown here, the results section 1102 has four subsections. The subsections include an air and bone conduction subsection 1112, a speech intelligibility subsection 1114, and a tympanogram/DP-OAE subsection 1116.

Figure 10A:
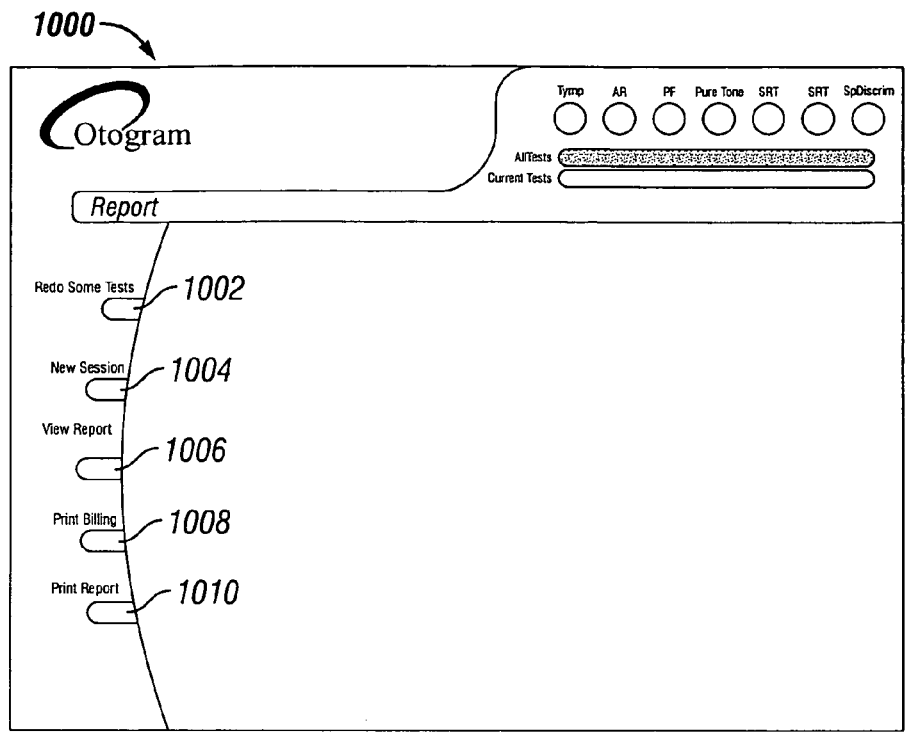
FIGS. 10A-10F illustrate an exemplary implementation of a reporting component of the user interface according to embodiments of the invention.
Figure 10B:
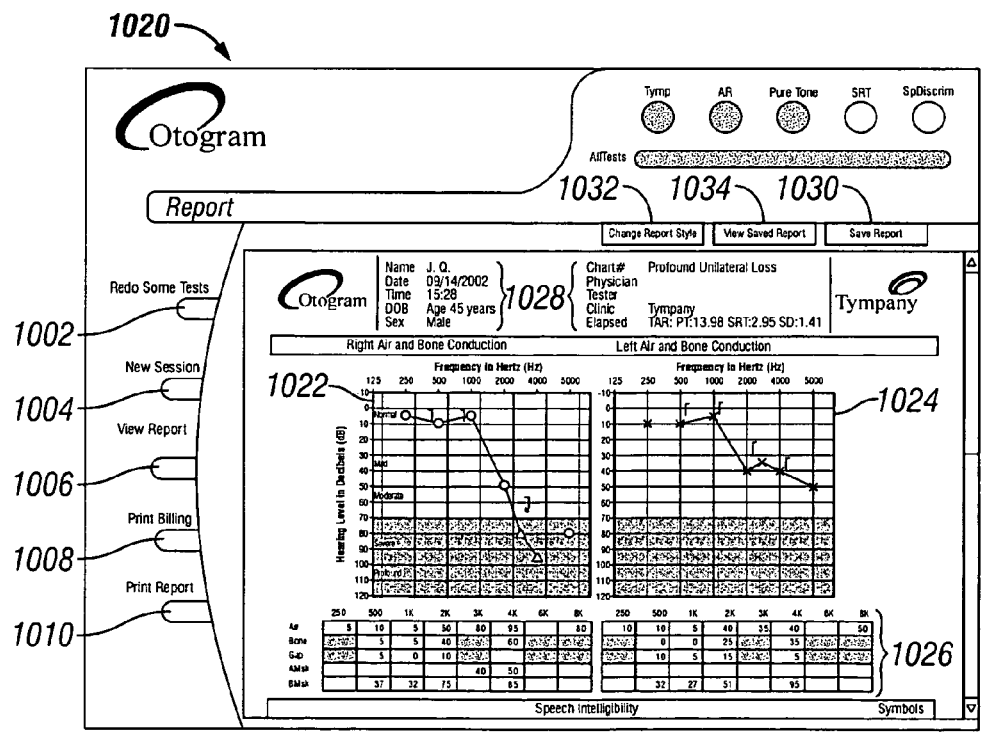
Figure 10C:
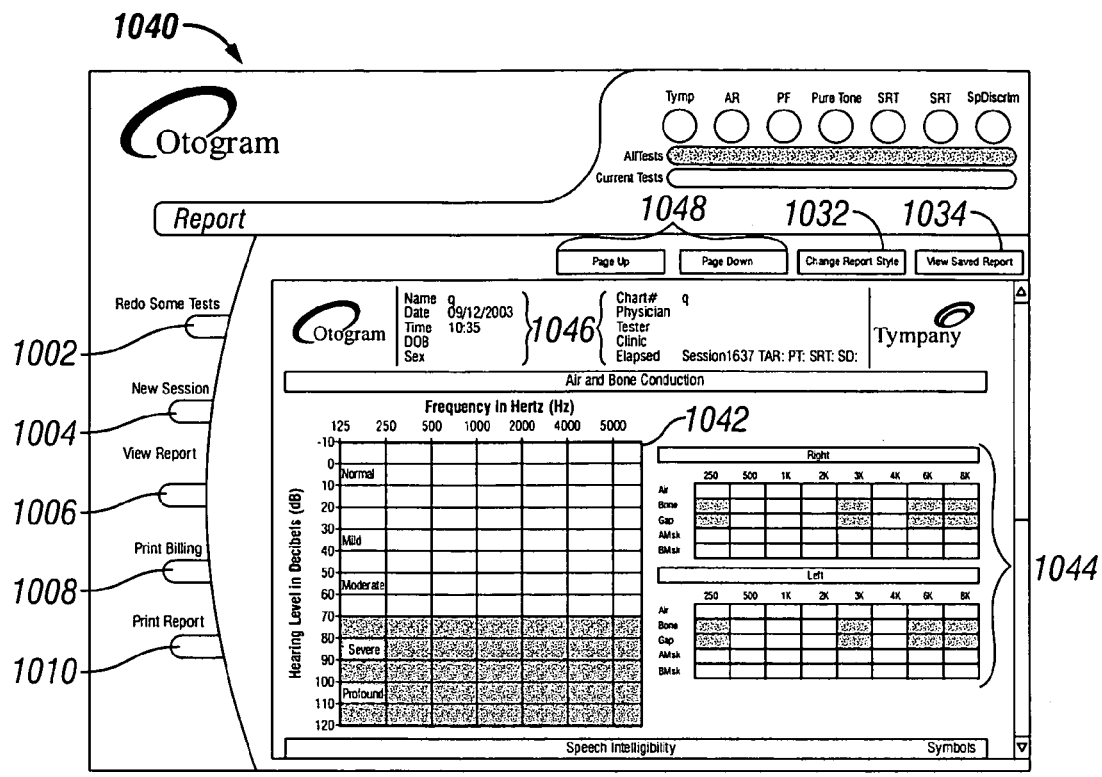
Figure 10D:
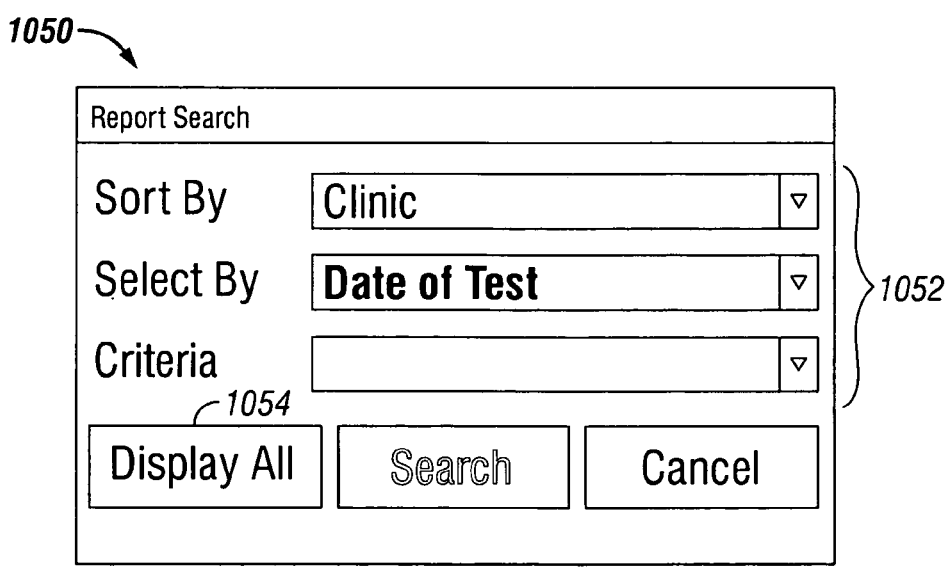
Figure 10E:
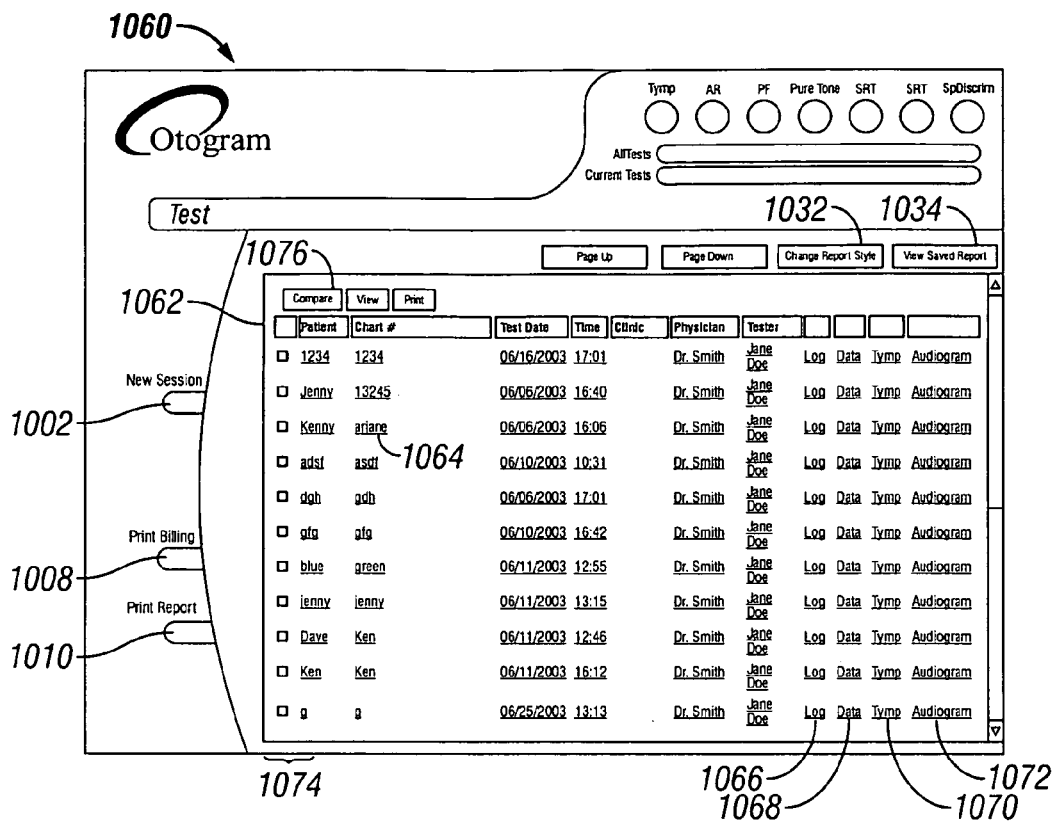
Figure 10F:
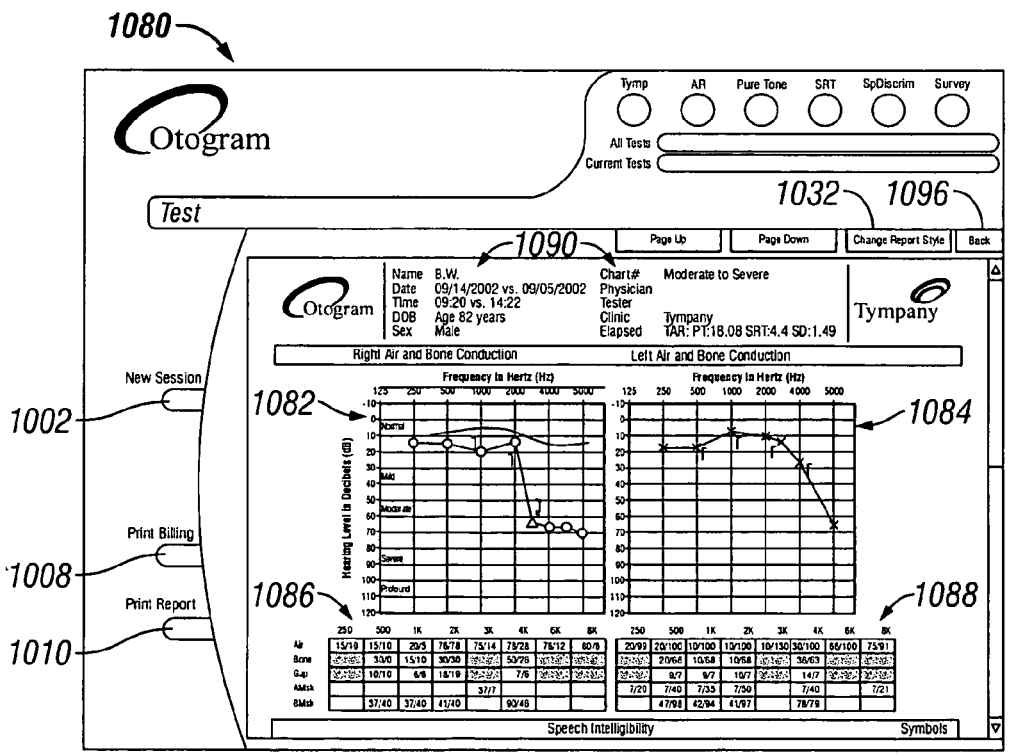

The first subsection, namely, the air and bone conduction subsection 1112, is similar to the one discussed previously with respect to the report screen 1020 (FIG. 10B). For example, information about the patient, generally indicated at 1120, is provided at the top of page. The results of the air and bone conduction test for the patient's right ear and left here are then provided via charts in a two-panel format. (It is also possible, of course, to report the results of the air and bone conduction test in a one-panel format with the data for both ears plotted in the same chart.) The right ear results are shown in the right chart 1122 and the left ear results are shown in the left chart 1124. The charts 1122 and 1124 are computer-generated audiograms that reflect the patient's performance for the air and bone conduction tests. The placement of the right chart 1122 on the left side and the left chart 1124 on the right side allows the audiologist or other hearing health professional to line up the charts with the patient's ears when facing the patient.

On the charts 1122 and 1124, the horizontal axis represents the frequency and the vertical axis represents the thresholds. In accordance with embodiments of the invention, the vertical axis is partitioned into five regions, including "normal," "mild," "moderate," "severe," and "profound." Each region indicates a distinct degree of hearing loss. Although five regions are shown here, it is possible to have fewer or more than five regions of hearing loss without departing from the scope of the invention. In some embodiments, each region of hearing loss may be shown in a different color, shading, or pattern in order to help the audiologist or other hearing health professional more clearly distinguish between the different regions. In some embodiments, the bone conduction data points may be surrounded by shading or otherwise highlighted to indicate a masking dilemma. A masking dilemma occurs when the minimum masking level required at the non-test ear also masks the test ear due to crossover, causing the thresholds in the test ear to be shifted.

The numerical data for each chart 1122 and 1124 is reported in table form at 1126 and 1128. Each row of the tables 1126 and 1128 displays a hearing threshold while each column represents a certain frequency. In the exemplary implementation shown here, there are five rows, including a row for the air conduction threshold, the bone conduction threshold, the air-bone gap, the air conduction threshold with masking, and the bone conduction threshold with masking. For each cell in the tables 1126 and 1128, the data may be displayed with certain indicators to indicate the quality and/or reliability level of the test results. For example, a superscripted "F" indicates that the patient's false response ratio, which is the number of false responses over the total number of responses, has exceeded a certain predefined limit (e.g., 40%). By way of background, a false response refers to a response that is received outside a predefined response window (i.e., the patient responded either too early or too late and is therefore considered to be guessing). A superscripted "T" indicates that the number of presentations required to obtain a threshold for the patient at a given frequency has exceeded a predefined limit (e.g., 18) considered to be a cutoff for good quality. A subscripted "NR" indicates that for some presentations, no response was received. And similarly to the charts 1122 and 1124, some bone conduction test results may be highlighted to indicate that the bone conduction loss prevented masking from being effectively presented. Another subscripted indicator, "U," indicates that masking was insufficient during the presentation. Blank cells indicate no data.

In some embodiments, a legend 1130 may also be present to explain the meaning of the various symbols and markers displayed in the air and bone conduction subsection 1112. The symbols are standard symbols used by most audiologist and hearing health professionals, but may certainly be modified as needed for a particular application.

The speech intelligibility subsection 1114 displays, again in table form, the results of the speech related hearing tests, including the speech reception threshold test and the speech discrimination test. For the speech reception threshold test, the speech intelligibility subsection 1114 displays the results of the average best pure-tone hearing within a speech range, the predicted SRT, and the lowest intensity level at which speech can still be understood by the patient. For the speech discrimination test, the speech intelligibility subsection 1114 displays the speech discrimination presentation level, the speech discrimination test score that is predicted by audibility factors alone, and the actual speech discrimination test score. (The audibility factors are based on the results of the patient's pure tone frequency thresholds.) In some embodiments, the speech intelligibility subsection 1114 also displays any speech discrimination loss that is not explained by the pure tone loss. This unexplained loss may be derived by subtracting the predicted speech discrimination test score and the actual speech discrimination test score.

In the exemplary implementation shown here, the speech intelligibility subsection 1114 includes a column for the description 1132 of each speech related test result described in the previous paragraph, a column for the measure 1134 used with each test (e.g., pure tone air conduction (PTA), SRT, etc.) along with a column for the units therefor, and a column for the results for the right ear 1136 and the left ear 1138. In some embodiments, the numbers in columns 1136 and 1138 may be shown with masking indicators, for example, a subscripted "msk" to indicate masking was presented and a superscripted number (e.g., "5") to indicate the intensity level of the masking. In some embodiments, the actual speech discrimination test score may be accompanied by the possible range of the testing error, as well understood by those having ordinary skill in the art.

The tympanogram/DP-OAE subsection 1116 presents the results of an acoustic admittance test (in the form of a tympanogram) and the DP-OAE test. In the exemplary implementation shown here, the tympanogram/DP-OAE subsection 1116 includes a tympanogram 1140 for the patient's right and left ears, reflecting the results of the acoustic admittance test. The numerical data for each ear is also reported in table form at 1142 and 1144 for the right and left ears, respectively, with the left column in each table listing the test type and the right column indicating the results. Another table displays the DP-OAE results at 1146 and 1148 for the right and left ears, respectively. As discussed above, the interpretive comments for the DP-OAE results are intended to indicate pass or fail for the individual scores as well as the overall results. In the example shown here, "OK" indicates a passing score and "X" indicates a failing score.

A comments subsection 1150 may also be present in some embodiments for providing interpretive comments about the tympanogram, for example, whether the tympanometry for each ear is "normal" or otherwise. The comments subsection 1150 may also provide an AMA (American Medical Association) hearing score in some embodiments that indicates the percentage of a disability that is caused by the patient's hearing loss. The AMA hearing score requires a pure tone threshold at 3 KHz in order to be able to calculate the score. If a threshold is not available at 3 KHz, then the automated hearing test uses data from available thresholds to extrapolate the 3 KHz threshold. The extrapolated threshold is then used to calculate an Estimated Person Impairment score that is similar, to and may be used in lieu of, the AMA hearing score. Where available, the comments subsection 1150 may also provide information regarding whether the patient has passed Stenger screening (e.g., "Stenger at 500 Hz is Negative," etc.). For information regarding Stenger screening in an automated hearing test, the reader is referred to U.S. Non-provisional application entitled "Stenger Screening in Automated Diagnostic Hearing Test," filed concurrently herewith, and incorporated herein by reference.

FIG. 11C shows an exemplary implementation of the test summary section 1104 for providing interpretive comments regarding various hearing related tests according to embodiments of the invention. As can be seen, the test summary section 1104 may include a table showing a description of the various tests at 1152 and the interpretive comments therefor for the right ear and the left ear, respectively, at 1154 and 1156. The test types may include, for example, the pure tone threshold test, SRT, speech discrimination test, tympanogram, DP-OAE. The interpretive comments for these tests may be the same as the ones discussed previously, or they may include other test types and interpretive comments as needed. The summary section 1104 may also note any asymmetries in the pure tone threshold test, SRT, and speech discrimination test, along with the interpretive comments therefor. In some embodiments, the results of the acoustic reflex test and the patient survey (e.g., the HHIE survey) may also be presented in this section. A synopsis of the various results and interpretive comments therefor may be provided with the summary table at 1158 in some embodiments.

In addition to the summary section 1104, FIG. 11C also shows an exemplary implementation of the medical recommendations section 1106. Again, the information is provided in the form of a table, with the types of recommendations listed in one column at 1160 and the recommendations themselves listed in another column at 1162. The various types of recommendations and the recommendations themselves may be the same as the ones discussed previously, or they may be a modified version, depending on the particular application.

As for the patient history section 1108, in some embodiments, the patient history section 1108 provides a list of possible symptoms that the patient may have experienced, indicated at 1164. The symptoms are typical symptoms, known to those of ordinary skill in the art, that a patient with hearing related problems may experience. An audiologist or other hearing health professional may then manually mark (e.g., "Yes" or "No") whether the patient has the symptoms for the right and left ears, as applicable, at 1166 and 1168, respectively. Comments may also be entered for each symptom at 1170 as needed.

Finally, the report 1100 may include one or more other sections 1110, such as a medical release section. The medical release section allows the audiologist or other hearing health professional to either refer the patient to a specialist for further treatment or to release the patient, for example, as having no contraindications that would affect fitting for a hearing aid. An example of a medical release is illustrated at 1110 in FIG. 11C. In some embodiments, billing information may also be presented in the report 1100, including information relating to the charges for the various hearing tests and other billing related information.

While the invention has been described with respect to a number of specific embodiments, those skilled in the art will recognize that the innovative concepts described herein can be modified and varied over a wide range of applications. Accordingly, the scope of the invention should not be limited to any of the specific exemplary teachings discussed, but is instead defined by the following claims.

What is claimed is:

1. A system for reporting a patient's hearing test results in an automated diagnostic hearing test, comprising:
   transducers, including an air conduction transducer and a bone conduction transducer;

a hearing test device connected to the transducers;

a computer connected to the hearing test device, the computer being programmed with and adapted to store a user interface for an automated hearing test, the user interface providing a graphical interface for the patient and configured to cause the computer to:

present the patient's hearing test results from the automated diagnostic hearing test on a graphical report, the graphical report including a plurality of graphical symbols, each graphical symbol representing a different aspect of the patient's hearing test results;

present one or more interpretive comments on the report regarding a degree of severity of the patient's hearing loss based on whether the patient's hearing test results satisfy one or more predefined criteria in a list of predefined criteria, the one or more interpretive comments being based upon a computer interpretation of the hearing test results and additionally pointing out possible inconsistencies, asymmetries, or areas of concern in the test results; and present one or more treatment solutions on the report based on the patient's hearing test results and the one or more interpretive comments.

2. The system according to claim, wherein the user interface is further configured to cause the computer to present one or more of the patient's hearing test in graphical form.

3. The system according to claim 1, wherein the user interface is further configured to cause the computer to present one or more of the following indicators with the patient's hearing test results: quality indicator, and reliability indicator.

4. The system according to claim 1, wherein the user interface is further configured to cause the computer to present one or more masking indicators with the patient's hearing test results.

5. The system according to claim 1, wherein the patient's hearing test results include results from at least one of the following tests: pure tone threshold, speech reception, speech discrimination, tympanogram, distortion product-otoacoustic emissions.

6. The system according to claim 1, wherein the interpretive comments include a type of hearing loss.

7. The system according to claim 6, wherein the type of hearing loss is derived based on a plurality of air-bone gap rules.

8. The system according to claim 1, wherein the automated diagnostic hearing test is configured to be initialized by the patient.

9. The system according to claim 1, wherein the automated diagnostic hearing test is performed on the patient without requiring any additional human intervention.

* * * * *